United States Patent [19]

Weil

[11] Patent Number: 4,839,275

[45] Date of Patent: Jun. 13, 1989

[54] CIRCULATING ANTIGENS OF DIROFILARIA IMMITIS, MONOCLONAL ANTIBODIES SPECIFIC THEREFOR AND METHODS OF PREPARING SUCH ANTIBODIES AND DETECTING SUCH ANTIGENS

[75] Inventor: Gary J. Weil, Creve Coeur, Mo.

[73] Assignee: The Jewish Hospital, St. Louis, Mo.

[21] Appl. No.: 814,684

[22] Filed: Dec. 30, 1985

Related U.S. Application Data

[63] Continuation-in-part of Ser. No. 730,728, May 6, 1985, which is a continuation of Ser. No. 557,117, Dec. 1, 1983, abandoned.

[51] Int. Cl.$^4$ ............... G01N 33/535; A61K 39/2; C07K 15/00
[52] U.S. Cl. .................. 435/7; 424/85.8; 424/88; 435/68; 435/172.2; 435/188; 435/240.27; 436/518; 436/543; 530/387; 530/395
[58] Field of Search .............. 530/387, 395; 424/85, 424/88, 117; 435/4, 7, 68, 70, 172.2, 188, 240, 241, 240.27; 935/89, 90, 92, 95, 103, 104, 106, 108, 110; 436/514–516, 518, 536–540, 543–548, 804, 806, 811

[56] References Cited

U.S. PATENT DOCUMENTS

| | | | |
|---|---|---|---|
| 4,322,495 | 3/1982 | Kato | 435/7 |
| 4,376,110 | 3/1983 | David et al. | 436/513 |
| 4,514,505 | 4/1985 | Canfield et al. | 436/500 |
| 4,568,639 | 2/1986 | Lew | 435/68 |
| 4,656,251 | 4/1987 | Mosier | 530/387 |
| 4,657,850 | 4/1987 | Grieve | 435/7 |

OTHER PUBLICATIONS

Hamilton, R. G. and Scott, A. L. American Journal of Veterinary Research, 45(10):2055–61(10–1984).
Cruickshank, J. K. et al, British Journal of Medicine, 283(6303):1349–1350 (1981).
Matsumura, K. et al, Immunology, 51:609–613 (1984).
Weil, G. J. et al, Amer. J. Trop. Med. Hyg. 33(3):425–430 (1984).
Fujita, K. et al, Tropical Medicine, 23(4):193–204 (12–1981).
Fujita, K. et al, Tropical Medicine, 24(4):219–228 (1982).
Scott, A. L. et al, Fed. Proc. 42:1089, Abst. 4673 (4–1983).
Des Moutis, I. et al, Amer. J. Trop. Med. Hygiene, 32:533–542 (1983).
Weil, G. et al, Fed. Proc. 42(4):852, Abst. 3281 (1983).
Tagawa, M. et al, Jap. J. Vet. Sci. 45(3):323–329 (1983).
Hayasaki, M. Jap. J. Vet. Sci. 43(1):21–26 (1981) cited in Bio. Abst. 72075622.
Roelants, G. E. et al, *The Immune System,* vol. 2, pp. 446–453 (Karger, Basel) (1981).
Pearson, T. W. et al, J. Immunol. Methods, 34:141–154 (1980).
Mitchell, G. F. et al, Austr. J. Exp. Biol. Med. Sci., 57:287–302 (1979).
Yoshida, N. et al, Science, 207:71–73 (1980).
Weil, G. J. et al, Amer. J. Trop. Med. Hyg. 31(3):477–485 (1982).

*Primary Examiner*—Margaret Moskowitz
*Attorney, Agent, or Firm*—Senniger, Powers, Leavitt and Roedel

[57] ABSTRACT

Novel hybrid cell lines are disclosed for providing monoclonal antibodies to circulating parasite antigens present in the blood of animals infected with the nematode parasite *Dirofilaria immitis.* Such circulating parasite antigens are also characterized and identified. Further disclosed are methods employed to produce and select such hybrid cell lines and diagnostically useful assay methods utilizing the monoclonal antibodies in the detection of such specific circulating parasite antigens in blood or bodily fluids.

14 Claims, 13 Drawing Sheets

FRACTION #

FRACTION #

1 2 3 4 5 6

1 2 3 4

CIRCULATING ANTIGENS OF DIROFILARIA IMMITIS, MONOCLONAL ANTIBODIES SPECIFIC THEREFOR AND METHODS OF PREPARING SUCH ANTIBODIES AND DETECTING SUCH ANTIGENS

REFERENCE TO CROSS-RELATED APPLICATIONS

This application is a continuation-in-part of application Ser. No. 730,728, filed May 6, 1985 which in turn is a continuation of application Ser. No. 557,117, filed Dec. 1, 1983, now abandoned.

BACKGROUND OF THE INVENTION

This invention relates generally to the nematode parasite *Dirofilaria immitis* and, more particularly, to newly characterized circulating parasite antigens present in the blood of animals infected with the nematode parasite *Dirofilaria immitis*, to novel hybrid cell lines that produce monoclonal antibodies to such parasite antigens, to the monoclonal antibodies themselves, and to diagnostic methods and compositions employing such antibodies in the detection of such previously uncharacterized specific parasite antigens as a means of diagnosing and quantifying parasitic infections.

*Dirofilaria immitis* (the common dog heartworm) is a filarial nematode parasite that is an important pathogen of canines in the United States and many other countries. Although the parasite can cause heart failure, lung disease and death, infected animals often have no outward evidence of disease. Signs of heartworm disease in dogs, when present, are nonspecific. The diagnosis of *D. immitis* infection is most commonly made by demonstrating microfilariae, larval forms of the parasite, in peripheral blood smears. This time-honored test is insensitive. It is now well recognized that a significant proportion of infected dogs lack microfilaremia. Microfilarial examination also suffers from a lack of specificity. Animals infected with nonpathogenic filarial parasites have circulating microfilariae that are difficult to distinguish from those of *D. immitis*. A number of serologic tests have been described that measure serum antibodies specific for parasite antigens as a means of diagnosing *D. immitis* infections. Unfortunately, these tests lack specificity. Uninfected dogs often have antibodies that react with *D. immitis* antigens because of prior infection, infection with related parasites, or exposure to the parasite without the development of mature infection.

A further difficulty with existing diagnostic techniques for *D. immitis* infection is that neither microfilarial counts nor antibody titers correlate significantly with the intensity of infection, the number of adult worms in the animal. Infection intensity may relate to the prognosis of infection in dogs with or without therapy. In summary, currently available parasitological and serological tests cannot reliably diagnose or quantitate *D. immitis* infections.

Difficulties with existing diagnostic techniques have inspired efforts to develop assays for parasite antigens that would have the potential of being sensitive, specific and related to infection intensity. The desire for antigen detection in parasitology is part of a general trend in microbiology toward assays that detect microbial antigen as a substitute for cultivation of the agent or measurement of antibody. Such assays have been particularly useful for pathogens that cannot be grown in vitro (i.e., Hepatitis B, rotovirus, Pneumocystis) or where rapid diagnosis of a serious illness can influence therapy before culture results are available (i.e., Cryptococcus, Hemophilus, or pneumococcal meningitis).

The first report of circulating parasite antigens in filariasis was published in 1946 by Franks (Journal of Parasitology, 32:400) who found that serum from filariasis patients caused a wheal and flare reaction when it was injected into skin that was passively sensitized with serum containing antifilarial antibodies. Thirty years later, Desowitz and Una (Journal of Helminthology, 50:53, 1976), who were using counterimmunoelectrophoresis (CIE) to measure antibody to *D. immitis* in dogs, reported the incidental finding that 2 of 5 infected dogs had circulating parasite antigen in serum. CIE has also been used to detect circulating parasite antigens in rats infected with filarial worms and in limited studies with human sera (e.g., see Dasgupta and Bala, Indian Journal of Medical Research, 67:30, 1978; and Kaliraj et al, Journal of Helminthology, 55:133, 1981). Until recently, however, no attempt had been made to identify the specific antigens that circulate in filarial infections or to develop more sensitive assays to detect such antigens.

In 1980, Ouassi et al. (American Journal of Tropical Medicine and Hygiene, 30:1211) developed a test for circulating onchocerciasis antigens based on polyvalent rabbit antiserum which detected antigenemia in 75% of infected patient sera. The major antigen detected was cathodic and trichloroacetic acid soluble. The same group more recently developed a monoclonal antibody specific for the circulating onchocerciasis antigen and they have successfully used the antibody to detect antigen in patient sera (Des Moutis et al., American Journal of Tropical Medicine and Hygiene, 32:533, 1983).

My own group (Weil et al., American Journal of Tropical Medicine and Hygiene, 33:425 (1984)) has focused on the canine-*Dirofilaria immitis* system, using counterimmunoelectrophoresis modified to increase sensitivity and detect antigens within immune complexes. Circulating antigens were detected in 24 of 24 infected dog sera independent of microfilarial patency. No false positive tests were observed in sera from 26 control dogs that were free of infection at necropsy or in sera from 13 dogs infected with the filarial worm *Dipetalonema reconditum*.

Hamilton et al. (Federation Proceedings, 43:854, 1983) have reported on efforts to detect circulating *D. immitis* antigens in dog sera with polyclonal (rabbit) antibody-based radioimmunoassays. They found that their ability to detect parasite antigens (unspecified and uncharacterized) was decreased in serum from dogs that contained high levels of specific antibody.

Scott et al. (Federation Proceedings, 42:1089, 1983) have reported the production of monoclonal antibodies to *Dirofilaria immitis* antigens obtained by fusing mouse myeloma cells with spleen cells of mice that had been immunized with *D. immitis* adult and microfilarial antigens. Two of the monoclonal antibodies were used together in an enzyme-linked immunosorbent assay (ELISA) to detect *D. immitis* antigens that had been added to normal dog sera with a sensitivity of 25 ng/ml. No description of the actual parasite antigens present within infected dog serum was provided. Similarly, there was no description of the detection of parasitic antigens in infected dog sera.

In the above-noted studies by Des Moutis et al. and Scott et al., monoclonal antibodies were produced by immunizing with crude antigen extracts and screening for antibody production either with TCA-extracted antigen (Des Moutis et al.) or the crude antigen extract (Scott et al.). To date there have been no reports on the nature of the parasite antigens that circulate in the serum of *D. immitis*-infected dogs. Accordingly, these antigens have not been characterized nor have monoclonal antibodies specific for such antigens been prepared as a means of diagnosing and quantifying parasitic infections caused by *D. immitis*.

SUMMARY OF THE INVENTION

Among the objects of the present invention may be noted the provision of newly identified and characterized circulating parasite antigens of *Dirofilaria immitis*; the provision of novel hybridoma cell lines that produce novel monoclonal antibodies specific to parasite antigens that circulate in the blood of infected animals; the provision of methods for preparing such hybridoma cell lines which involve the use of new techniques; the provision of such novel monoclonal antibodies further characterized by a determination of isotypes, assessment of antigen specificity and ability to precipitate antigen; and the provision of diagnostic assays for detecting the presence of circulating parasite antigens of *Dirofilaria immitis* in the serum of infected dogs. Other objects and features will be in part apparent and in part pointed out hereinafter.

Briefly, the present invention is directed to circulating parasite antigens of *Dirofilaria immitis* newly characterized as having these properties: (a) the antigens being present in *Dirofilaria immitis* worms and in the serum of animals infected with *Dirofilaria immitis*; (b) being high molecular weight parasite antigens in infected dog sera as demonstrated by the immunoblot method with polyclonal and monoclonal antibodies; (c) not being destroyed by trichloroacetic acid extraction or by perchloric acid extraction; (d) not being destroyed by heat treatment at approximately 100° C. for 30 minutes; (e) having isoelectric points of under 4 as determined by a combination of ion exchange chromatography and rocket-line immunoelectrophoresis; (f) migrating towards the anode at pH 8.6 in agarose gel (10 V/cm) with migration distances relative to albumin of 1.1 and about 1.0 as determined by crossed immunoelectrophoresis; (g) forming lines of identity in rocket-line immunoelectrophoresis with soluble acid and heat-stable antigens extracted from adult *D. immitis* worms; (h) being a subset of antigens produced in vitro by adult female *D. immitis* worms; (i) having a phosphocholine determinant; and (j) having determinants whose immunoreactivity is ablated by treatment thereof with sodium metaperiodate.

The invention is also directed to monoclonal antibodies produced by hybridoma cell lines formed by fusion of cells from a mouse myeloma line and spleen cells from a mouse previously immunized with an antigenic extract prepared from the nematode parasite *Dirofilaria immitis*, which antibodies bind to antigenic determinants of circulating parasite antigens of *Dirofilaria immitis* found in the serum of infected dogs and further characterized by binding strongly to the uterine wall and to the eggs of *Dirofilaria immitis* female adult worms.

In another aspect, the invention is concerned with a method for preparing such monoclonal antibodies which utilizes a sequence of steps including the novel technique of selecting, screening and cloning a hybridoma cell line producing the desired antibodies by means of enzyme-linked immunosorbent assay (ELISA) and counterimmunoelectrophoresis (CIE) inhibition procedures.

In still another aspect, the invention is directed to an assay method for determining the presence of circulating parasite antigens of *Dirofilaria immitis*, as above characterized, in a sample of serum from a dog infected with *Dirofilaria immitis* by analyzing the sample for the presence of such antigens by means of immunologic techniques whereby the presence of the parasite antigens may be detected.

A.—Crossed immunoelectrophoresis of DATH vs. rabbit anti-*D. immitis*.

Figure 3:
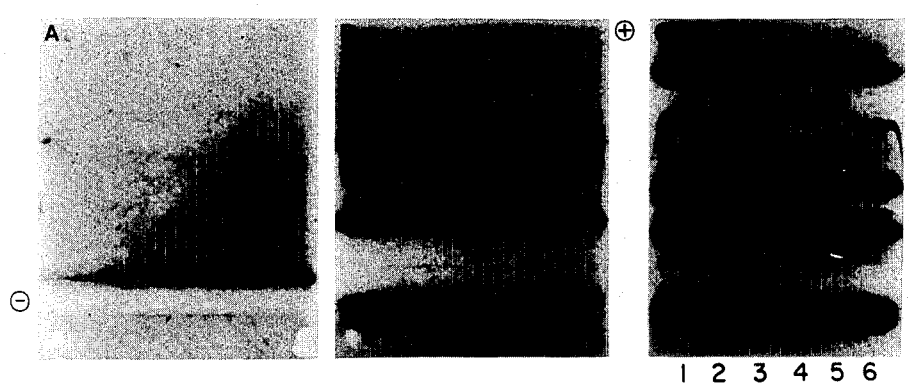

B.—Tandem crossed immunoelectrophoresis of DATH (left) and parasite antigen derived from dog serum (right);

FIG. 3 shows parasite antigens derived from dog serum analyzed by:

A.—Crossed immunoelectrophoresis.

B.—Crossed-line immunoelectrophoresis, DATH in the antigen strip.

C.—Rocket-line electrophoresis, DATH in the antigen strip.

Figure 4A:
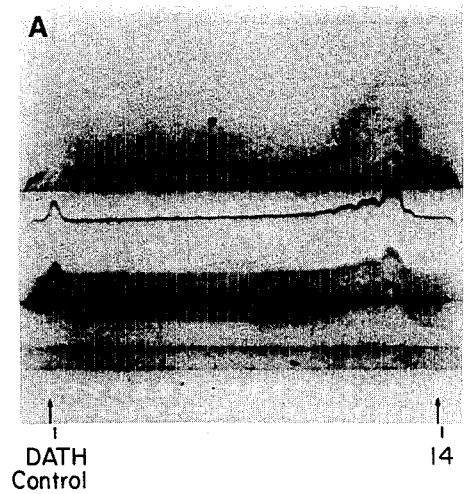
Figure 4B:
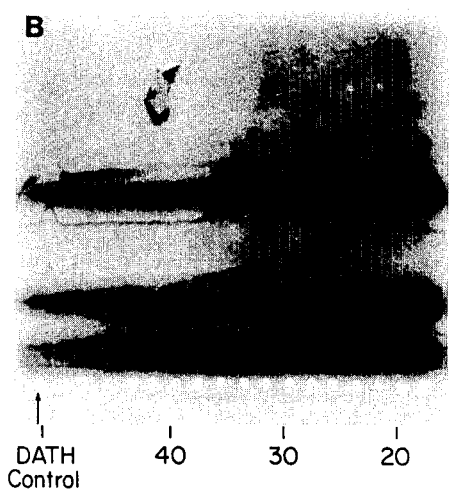
Figure 5:
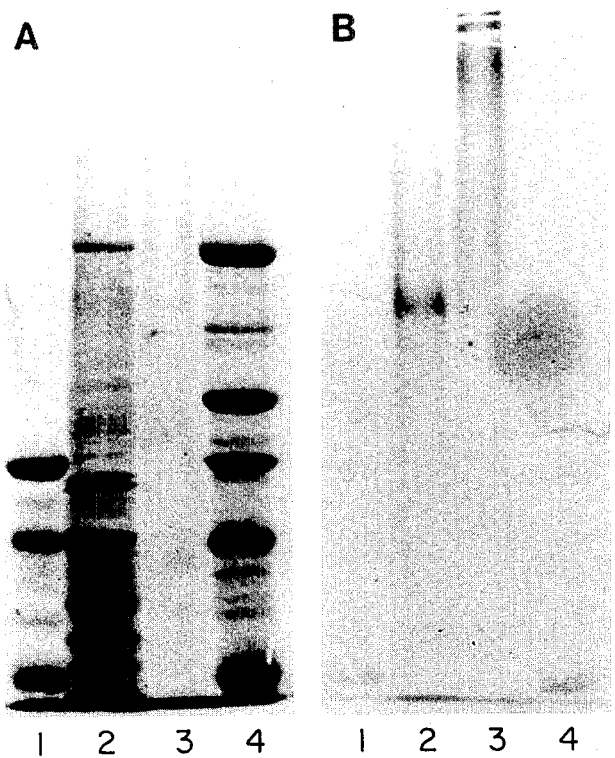

1. *D. immitis* adult male antigen, 6.0 ug. protein applied.
2. *D. immitis* adult female antigen, 1.25 ug. 3. *D. immitis* microfilarial antigen, 7.5 ug. 4. Serum derived antigen, approximately 50 fold concentrated. 5. DATH, 0.25 ug. 6. PBS;

FIG. 4A shows the rocket-line electrophoresis elution profile of DATH from a P-100 (Biorad Laboratories, Richmond, Calif.) gel filtration column, 0.7×50 cm, 11 ml/hr. Rover 1 and Rover 2 eluted with blue dextran;

FIG. 4B shows the elution profile of DATH from a Sephacryl S-300 column (Pharmacia). Column 50×1 cm, flow 6 ml/hr. Blue dextran, peak fx 26; ferritin, peak fx 33; B-12, peak fx 58;

FIG. 5 depicts the results of SDS-polyacrylamide gel electrophoresis (5%, reducing conditions) of *D. immitis* antigens.

A.—Coomassie blue stain. Lanes 1, 4, MW markers (myosin, b-galactosidase, phosphorylase b, bovine serum albumin, ovalbumin). Lane 2, *D. immitis* adult antigen. Lane 3, DATH.

Figure 6:
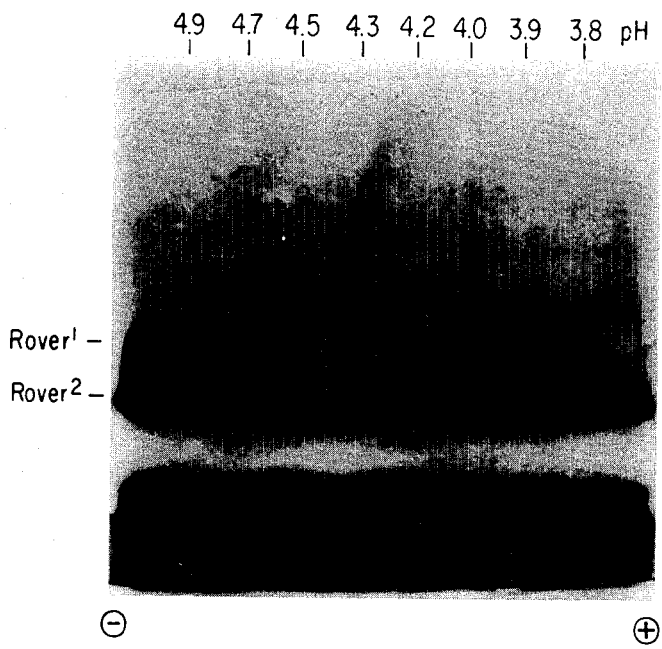
Figure 7:
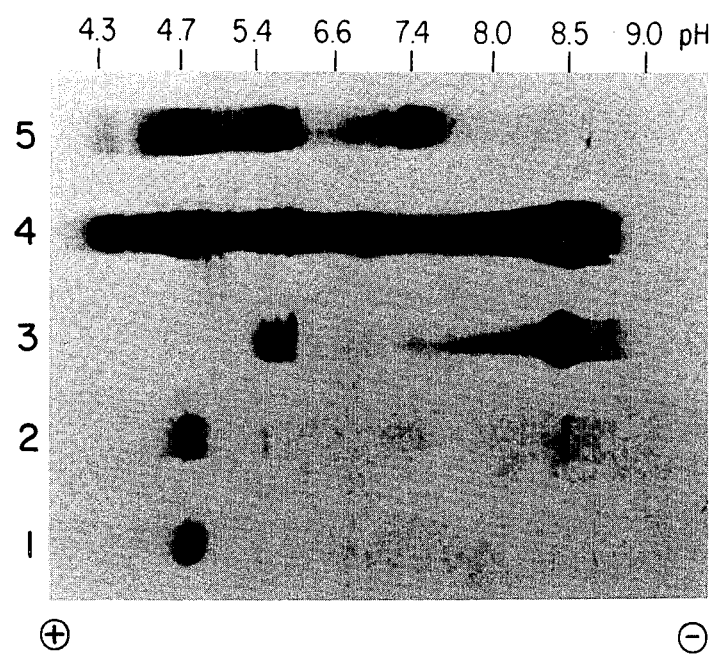
Figure 8A:
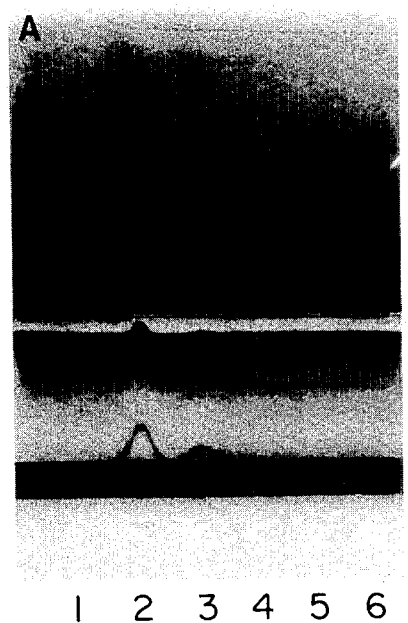
Figure 8B:
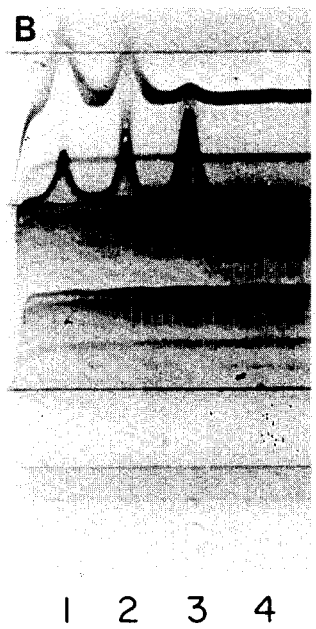

B.—PAS stain of duplicate gel;

FIG. 6 depicts the results of crossed-line immunoelectrofocus gel of DATH. DATH was focused in agarose using 2% ampholyte (pH range 3-5, LKB, Rockville, Md.). A lane containing focused antigen was then used as the first dimension in crossed-line immunoelectrophoresis vs. rabbit anti-*D. immitis* antiserum with DATH in the antigen strip;

FIG. 7 shows isoelectric focusing in agarose of monoclonal antibodies (2% ampholyte, pH 3.5–10, 6 W constant power, 90 minutes). Lane 1, BSA (Sigma); 2. Ammonium sulfate concentrated culture supernatant of cell line 1418BF2.1 cultured in serum-free medium (HB101, Hana Biologicals, Berkeley, Calif.); 3. Cell line 1418BF2.1 ascites after ammonium sulfate and DEAE cellulose treatment; 4. Cell line 1418BF2.1 ascites after ammonium sulfate precipitation; 5. Normal mouse serum;

FIG. 8A shows the results of rocket-line electrophoresis (DATH in antigen strip) of DATH fractions eluted from a monoclonal 1418BF2.1 affinity column. 1. PBS. 2. DATH. 3. DATH after incubation with antibody beads. 4. Washed beads eluted with 0.5M NaSCN in PBS. 5. Beads eluted with 3.5M NaSCN. 6. Beads eluted with 0.1M glycine, pH 2.5;

FIG. 8B shows the results of rocket-line electrophoresis of heat-treated immunoprecipitates of DATH, monoclonal antibodies. Antigen strip contained *D. immitis* adult antigens, and affinity purified sheep anti mouse antibodies. 1. DATH. 2. 1419BA12.1. 3. 1418BF2.1. 4. Normal mouse serum.

Figure 9:
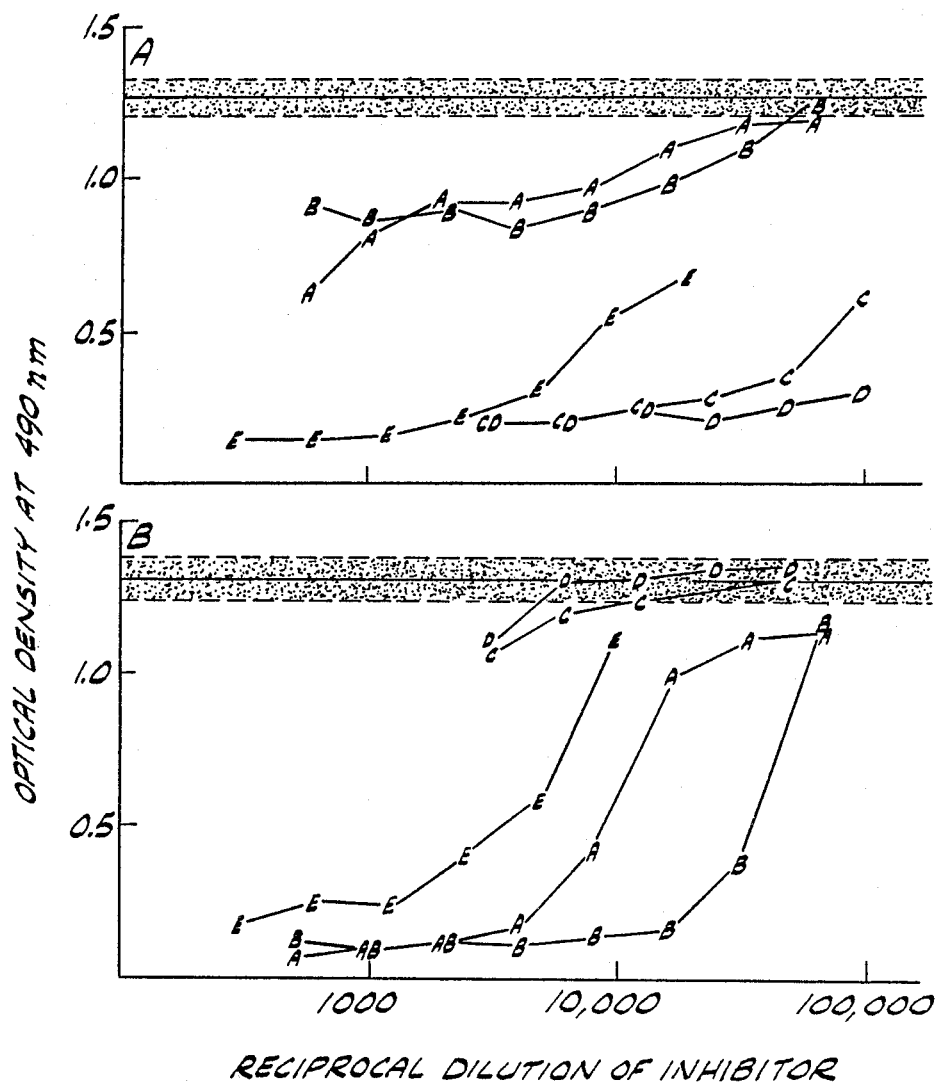
Figure 9A:
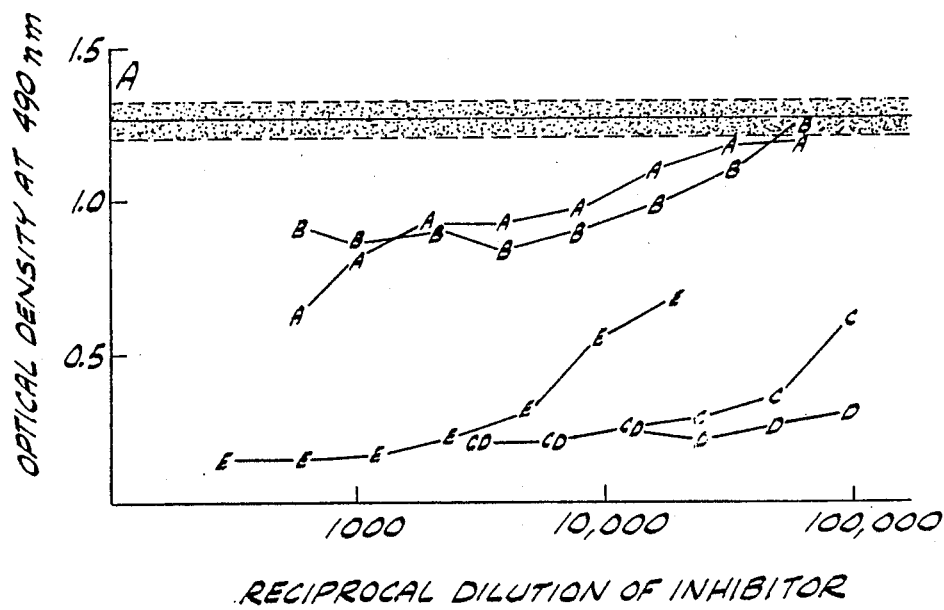

FIG. 9A shows the inhibition of binding of labeled monoclonal 1418BF2.1 to DATH by unlabeled monoclonals or rabbit antiserum. Shaded zone is diluent control +/− S.D. A. 1419DB6.2; B. 1419BA12.1; C. 1418BA10.1; D. 1418BF2.1; E. Rabbit anti-*D. immitis* serum.

Figure 9B:
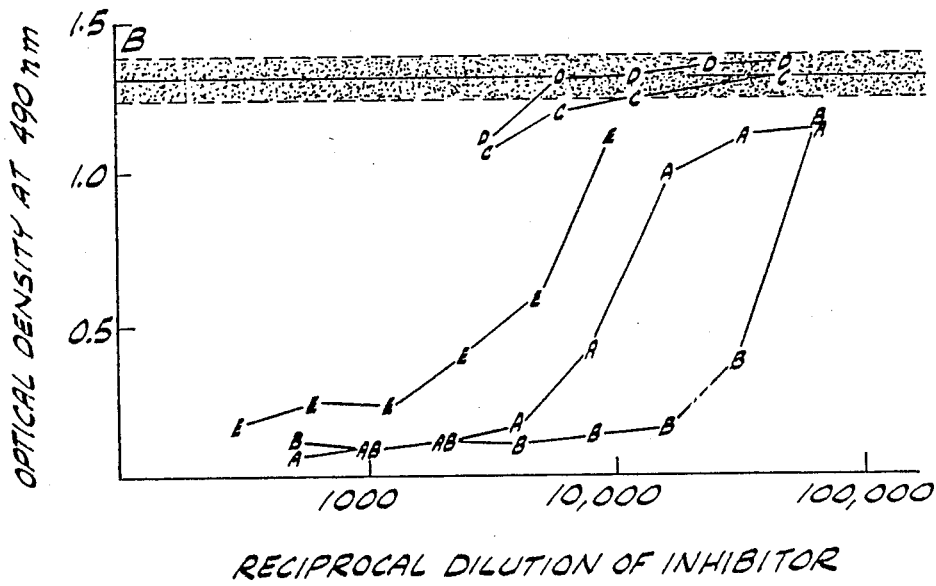
Figure 10:
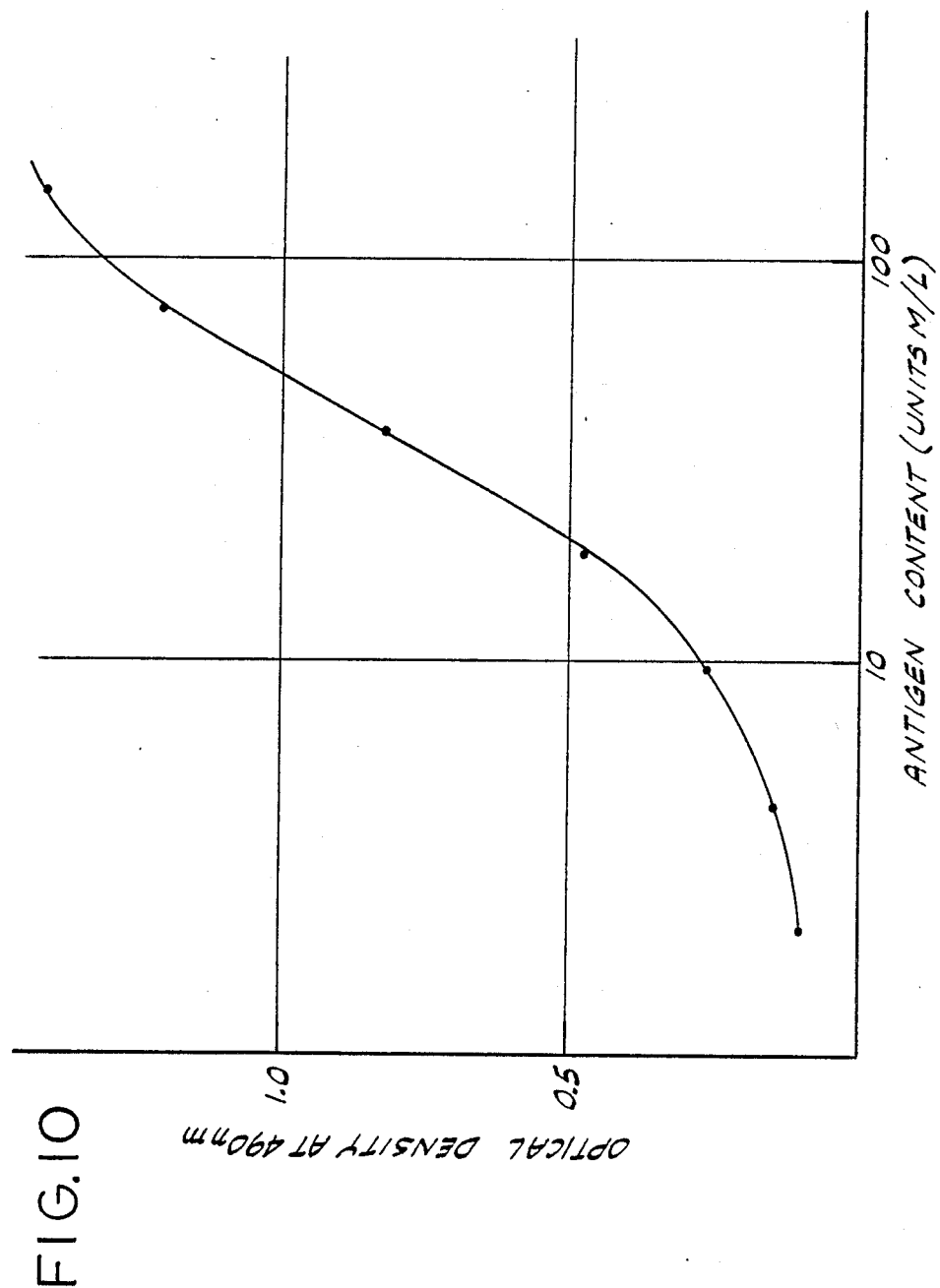
Figure 11:
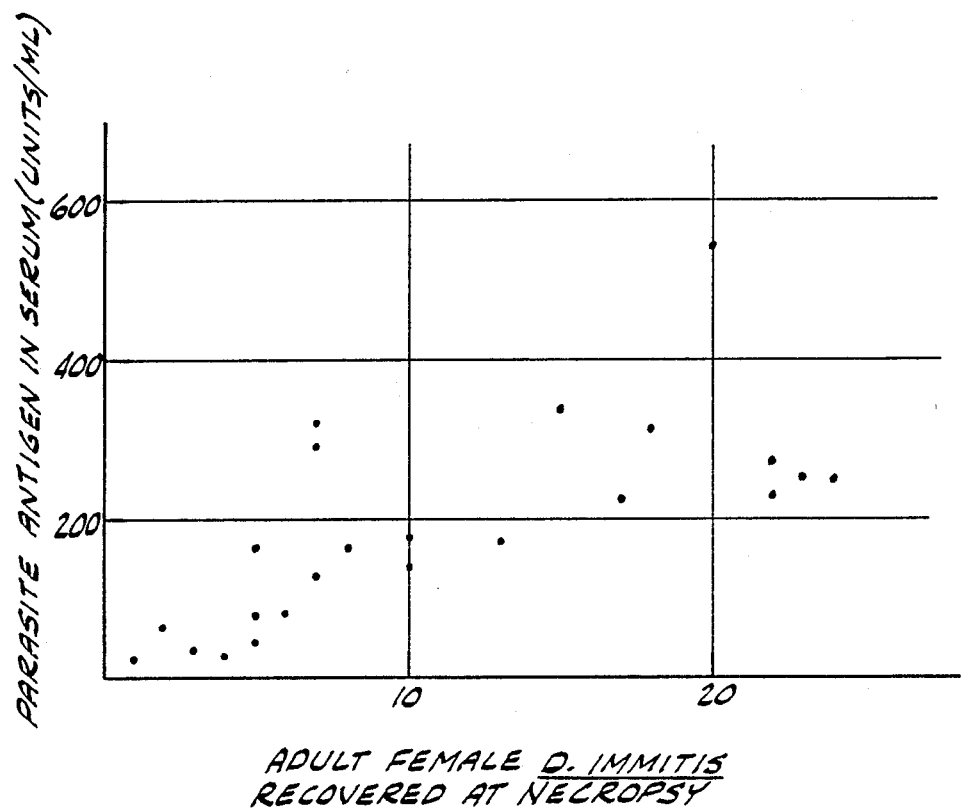
Figure 12:
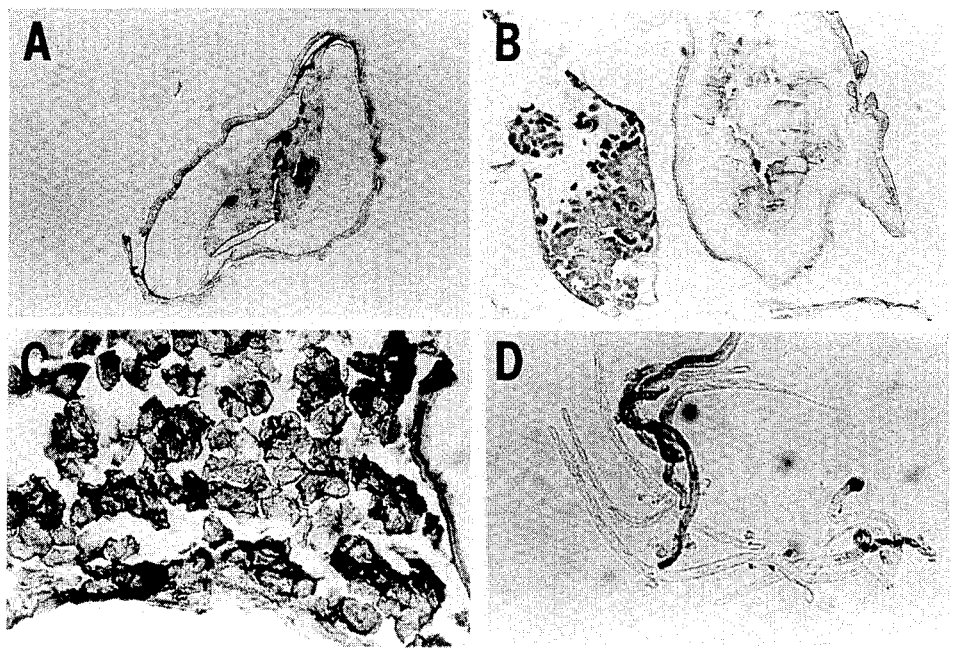
Figure 13:
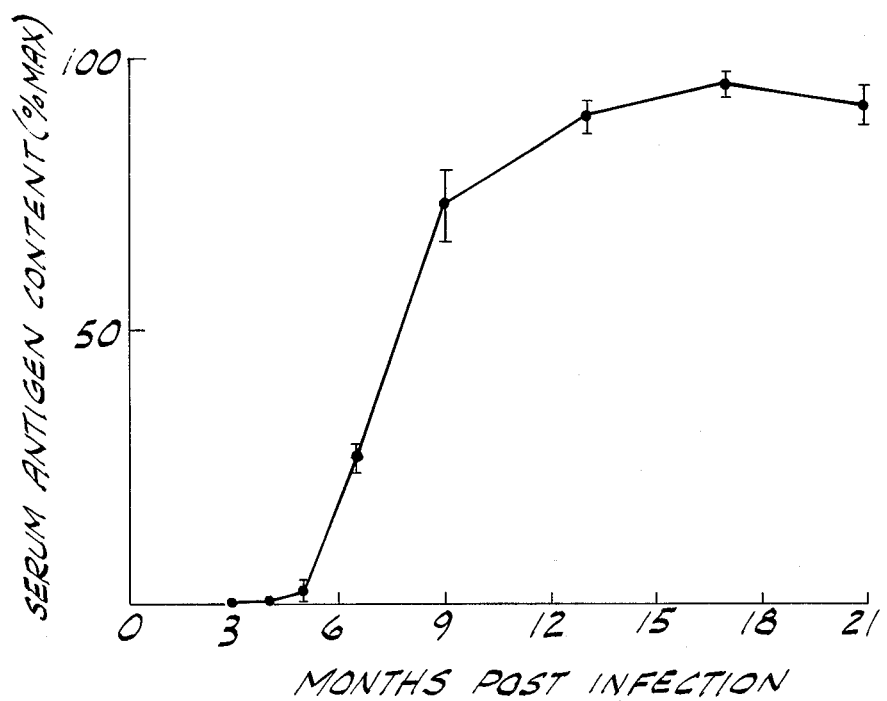
Figure 14A:
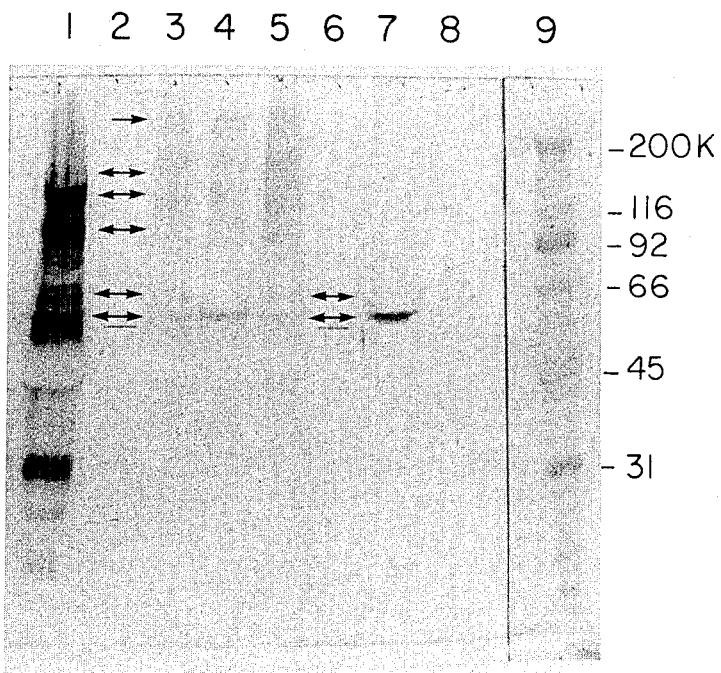
Figure 14B:
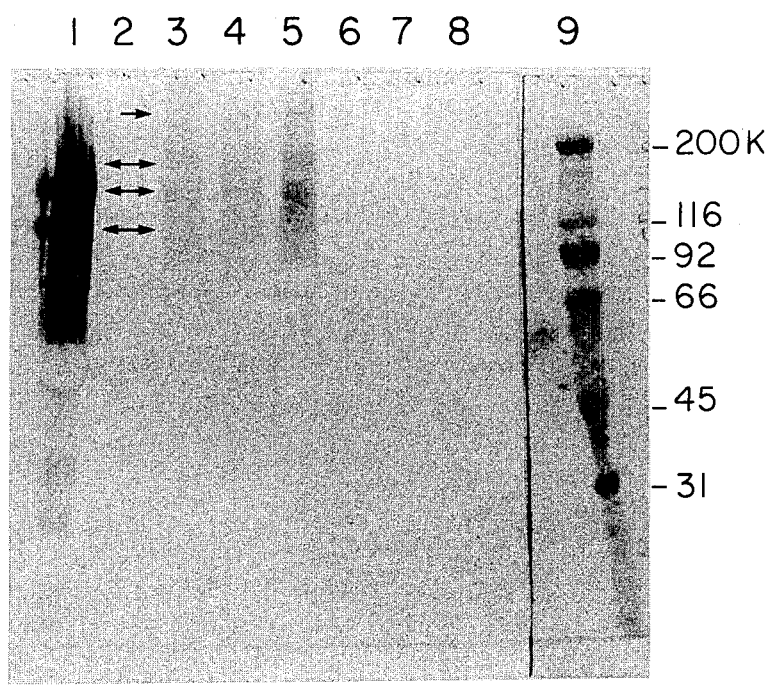
Figure 15:
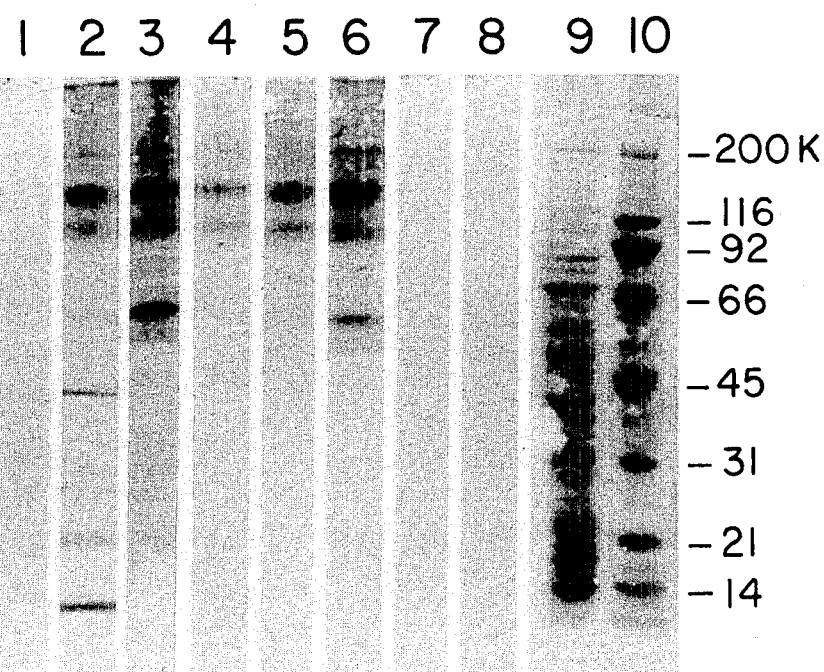
Figure 16:
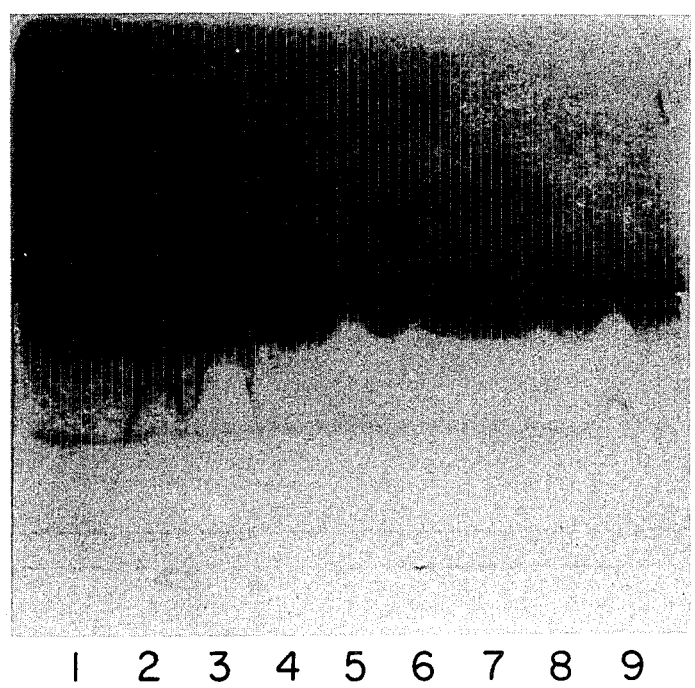
Figure 17:
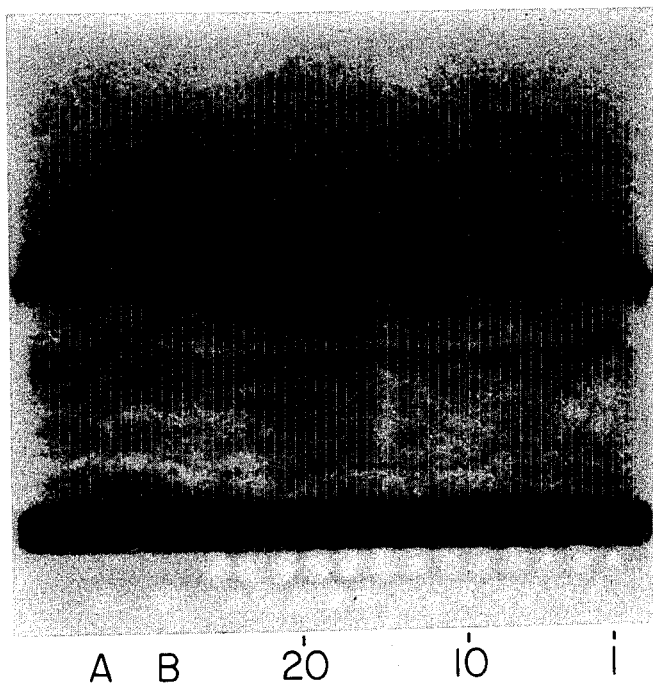

FIG. 9B shows the inhibition of binding of labeled monoclonal 1419BA12.1 to DATH by unlabeled monoclonals or rabbit antiserum. Letters have same meanings as in FIG. 9A;

FIG. 10 is a representative standard curve for the detection of circulating antigens of *D. immitis* using monoclonal antibody 1418BF2.1. The graph shows antigen units (DATH protein content, ng/ml) vs. optical density at 490 nm;

FIG. 11 is a graphic representation of serum parasite antigen content vs. number of female worms recovered at necropsy (Pearson correlation coefficient, r=0.70, P less than 0.001);

FIG. 12 shows the localization of monoclonal 1418BF2.1 binding sites in *D. immitis* worms by immunoperoxidase labeling. A. Adult male, 50×; B. Adult female, uterine segment on left, 50×; C. Adult female, uterus, 250×; D. Microfilariae, 250×;

FIG. 13 is a graphic representation of the time course of parasite antigenemia for 8 dogs experimentally infected with *D. immitis*. Ordinate represents mean (±S.E.) of antigen content expressed as % of the maximum value observed for each dog;

FIGS. 14A and 14B provide an immunoblot demonstration of *D. immitis* antigen in infected dog sera detected by rabbit anti-*D. immitis* antibodies (FIG. 14A), and by monoclonal antibody 1418BF2.1 (FIG. 14B). Lane 1, female-ES; 2, blank; 3–5, sera from 3 infected dogs; 6 blank; 7–8, sera from uninfected dogs; 9, molecular weight markers;

FIG. 15 shows the results of an immunoblot analysis of monoclonal antibody binding to *Dirofilaria immitis* antigen. Lane 1, normal mouse serum; lane 2, immune mouse serum; lane 3, monoclonal antibody 1418BF2.1; lane 4, monoclonal antibody 1419BA12.1; lane 5, monoclonal antibody 1419DB6.2; lane 6, monoclonal antibody 1418BA10.1; lane 7, unrelated monoclonal antibody control; lane 8, conjugate control; lane 9, *D. immitis* adult antigen, protein stain; lane 10, molecular weight markers, protein stain;

FIG. 16 shows the results of rocket-line immunoelectrophoresis with DiA-TCA/heat in the antigen strip and rabbit anti-DiA antibodies in the antibody gel. 1, RPMI-1640; 2, female-ES; 3, male-ES; 4, MF-ES; 5 and 6, two infected dog sera concentrated 5-fold after TCA and heat treatment; 7, uninfected dog serum concentrated 5-fold after TCA and heat treatment; 9, DiA-TCA heat after DEAE-cellulose treatment; 8, DiA-TCA/heat (positive control). Rover 1 and Rover 2 are the top two horizontal antigen lines visible in the photograph; and FIG. 17 shows the results of fused rocket-line immunoelectrophoresis (DiA-TCA/heat in the antigen strip, rabbit anti-*D. immitis* antibody gel) used to monitor antigen content in fractions eluted from a DEAE-cellulose column loaded with DiA-TCA/heat. Fractions 1–5 (1 ml each) were eluted with starting buffer, 0.1M acetate buffer, pH 4.0. Fractions 6–25 (0.5 ml each) were eluted with acetate buffer with a NaCl linear gradient (0–1.1M). Well A, DiA-TCA/heat; well B, starting buffer. Rover 1 and Rover 2 are the top two horizontal antigen lines visible in FIG. 17.

DESCRIPTION OF THE PREFERRED EMBODIMENTS

In accordance with the present invention, I have identified circulating parasite antigens of *Dirofilaria immitis* present in the serum of *D. immitis* infected dogs and characterized the antigens to the extent necessary to distinguish these antigens from other antigens, such as the circulating onchocerciasis antigen described by Ouassi et al. and Des Moutis et al., supra, and thereby render it possible to detect these specific antigens in the serum of *D. immitis* infected dogs. Thus, I have found that these newly characterized circulating parasite antigens of *Dirofilaria immitis* partially purified and isolated from *Dirofilaria immitis* adult worms or infected dog serum have the following properties:

(a) the antigens being present in *Dirofilaria immitis* worms and in the serum of animals infected with *Dirofilaria immitis*;

(b) being high molecular weight parasite antigens in infected dog sera as demonstrated by the immunoblot method with polyclonal and monoclonal antibodies;

(c) not being destroyed by trichloroacetic acid extraction or by perchloric acid extraction;

(d) not being destroyed by heat treatment at approximately 100° C. for 30 minutes;

(e) having isoelectric points of under 4 as determined by a combination of ion exchange chromatography and rocket-line immunoelectrophoresis;

(f) migrating towards the anode at pH 8.6 in agarose gel (10 V/cm) with migration distances relative to albumin of 1.1 and about 1.0 as determined by crossed immunoelectrophoresis;

(g) forming lines of identity in rocket-line immunoelectrophoresis with soluble acid and heat-stable antigens extracted from adult *D. immitis* worms;

(h) being a subset of antigens produced in vitro by adult female *D. immitis* worms;

(i) having a phosphocholine determinant; and (j) having determinants whose immunoreactivity is ablated by treatment thereof with sodium metaperiodate.

The experimental determination of these characteristics of circulating parasite antigens of *Dirofilaria immitis* (specifically designated Rover 1 and Rover 2) is set forth in detail hereinafter. Reference to these newly characterized antigens herein includes the antigens and their constituent epitopes and other antigens containing these epitopes or degradation products of such antigens containing these epitopes and which are recognized by the monoclonal antibodies of the invention.

As shown hereinafter, a variety of methods were used to identify and characterize these antigens. Two antigens were identified in infected dog sera that formed lines of identity in rocket-line immunoelectrophoresis with soluble antigens extracted from adult *D. immitis*. Biochemical analysis of these worm antigens suggested that they were acidic proteoglycans. Circulating *D. immitis* antigens were also demonstrated in infected dog sera by immunoblot analysis with polyclonal and monoclonal antibodies. Studies of parasite antigens released during in vitro culture indicated that the circulating *D. immitis* antigens in dog sera are primarily derived from adult female worms.

In further accordance with the invention, there is provided methods for the production, screening and selection of hybridoma cell lines that produce monoclonal antibodies specific for circulating parasite antigens of *Dirofilaria immitis*. These methods involve first immunizing mice with an antigenic extract prepared from the nematode parasite *Dirofilaria immitis*. This extract may be in purified or unpurified form. Preferably, it is a purified extract prepared from adult worms by extraction thereof with trichloroacetic acid (TCA) and heat treatment at approximately 100° C. for 30 minutes, such TCA and heat treated extract being referred to herein as DATH or DiA-TCA/heat.

The method next involves removing spleens from the mice and making a suspension of the spleen cells, fusing the spleen cells with mouse myeloma cells in the presence of a fusion promoter, diluting and culturing the fused cells in separate wells in a medium which will not support the unfused myeloma cells, and evaluating the supernatant in each well containing a hybridoma for the presence of the desired antibodies. At this point, the method of the invention includes the improvement which involves screening, selecting, and cloning hybridoma cell lines producing the desired monoclonal antibodies by the novel means of enzyme-linked immunosorbent assay (ELISA) and counterimmunoelectrophoresis (CIE) inhibition procedures. The novel hybridoma cell lines thus produced may then be employed to prepare the desired monoclonal antibodies by in vitro cultivation or by transferring the clones into mice and harvesting the desired monoclonal antibodies contained in the ascites or serum from the mice. The preparation of the monoclonal antibodies of the invention is described in detail below and, as noted, two of the monoclonal antibodies prepared were of the IgG$_1$ isotype and two were of the IgM isotype. It will be understood that other monoclonal antibodies which are specific for determinants present in *Dirofilaria immitis* circulating parasite antigens found in the serum of *D. immitis* infected dogs or which recognize the aforementioned characterized circulating parasite antigens are also within the purview of the present invention.

Another important embodiment of the present invention resides in the provision of an assay for *Dirofilaria immitis* infection in animals, notably dogs. In general and in its broadest aspect, the assay involves providing a sample of serum from a dog infected with or suspected of being infected with *Dirofilaria immitis* and analyzing the same for the presence of the aforementioned and herein characterized circulating parasite antigens of *Dirofilaria immitis* by means of immunologic techniques using the monoclonal antibodies of the invention or polyclonal or polyvalent antibodies. Thus, the identification and characterization of the circulating parasite antigens of *Dirofilaria immitis* as described herein in accordance with the invention likewise renders possible their detection by means of such assay techniques in order to diagnose filarial infections.

More specifically, the assay of the invention may be carried out by combining a sample of blood or bodily fluid from an animal infected with or suspected of being infected with *Dirofilaria immitis* with a monoclonal antibody of the invention specific for circulating parasite antigens of *Dirofilaria immitis*, the monoclonal antibody being in either its native (unmodified) state or chemically modified state whereby the presence of such antigens can be readily determined. Where a monoclonal antibody of the invention is employed in modified form, it may be labeled for example with an enzyme which provides a detectible signal, with the presence of the circulating parasite antigens being detected by means of such signal. It will be understood that the monoclonal antibodies of the invention may be labeled with a wide variety of labels conventionally employed in counting and in diagnostic assays. Such labels may include, but are not limited to, radioactive labels, fluorescent compounds, enzymes, biotin, ferromagnetic labels or the like. In each instance, the binding of the monoclonal antibody to the binding sites or determinants present on the circulating parasite antigens found in the serum of *D. immitis* infected dogs or constituent epitopes thereof will provide for detection of and assaying for the presence of the antigens. In lieu of the monoclonal antibodies of the invention but less advantageously, polyvalent or polyclonal antibodies may be utilized and be similarly labeled to provide a detectible signal in the conventional manner.

The monoclonal antibodies of the invention may also be employed in unmodified or native form for carrying out assays for determining the presence of circulating parasite antigens of *Dirofilaria immitis* by double antibody assay (e.g., sandwich ELISA assay) techniques known to the art. In such techniques, the monoclonals may be used as both the first and second antibodies or as the first antibody with a labeled polyclonal antibody being used as the second antibody or vice versa.

In one practical embodiment of the sandwich ELISA assay, for example, a rabbit polyclonal antibody directed towards the circulating parasite antigens of *Dirofilaria immitis* is attached to a solid support. The sample of serum from a dog infected with *Dirofilaria immitis* and a horseradish peroxidase conjugated monoclonal antibody specific for determinants present on such circulating parasite antigens is added to the solid support and allowed to react. If the circulating parasite antigens are present in the sample, a polyclonal antibody-antigen-conjugated monoclonal antibody sandwich is formed which following addition of a horseradish peroxidase substrate will develop color. This color is subjectively or quantitatively compared to standards by the user and a determination of the presence or absence of the circulating parasite antigens is made.

As shown by the experimental work detailed hereinafter, I have identified two antigens in trichloracetic acid-heat treated extracts which are highly cross-reactive with the circulating antigens on the basis of rocket-line electrophoresis. These antigens have been further purified by ion exchange chromatography and have been chemically characterized as acidic proteoglycans. Also, as shown below, the circulating antigens have been identified in the serum of *D. immitis* infected dogs, have a phosphocholine determinant and are characterized by having determinants whose immunoreactivity is ablated by treatment with sodium metaperiodate.

The monoclonal antibodies of the invention bind to determinants present on *Dirofilaria immitis* circulating antigens found in the serum of *D. immitis* dogs. These antigens can be detected with antiphosphocholine monoclonal antibodies, but other monoclonal antibodies of the invention that bind to the circulating antigens are not specific for phosphocholine. The epitope or determinant specificity of these monoclonal antibodies is presently unknown. Binding sites for these antibodies have been identified in the parasites, there being strong binding to the female uterine wall and to the eggs, including both the egg contents and the vitelline membrane.

As demonstrated by the test results shown below, the sensitivity and specificity of the monoclonal antibody-based antigen assay of the invention are markedly superior to prior art tests for canine dirofilariasis which are based on detection of microfilariae in blood or the measurement of antibody to parasite antigens. The assay of the invention exhibits the desired parasite specificity and does not detect parasite antigen in sera from dogs infected with the filarial nematode *Dipetalonema reconditum*, or in sera from humans infected with *Wuchereria bancrofti* or *Onchocerca volvulus*.

The specific assay described in detail below is an illustrative assay for *Dirofilaria immitis* infection in dogs or for the detection of circulating *D. immitis* antigens by monoclonal antibody-based assay to diagnose *D. immitis* infections in dogs, but it will be understood from the foregoing that the practice of the invention is not limited to such a specific embodiment.

Experimental

The following illustrates the practice of the invention.

EXAMPLE 1

Identification of Circulating Parasite Antigens in Sera from *D. Immitis*-Infected Dogs Preliminary work was performed to identify and partially characterize the parasite antigens that circulate in *D. immitis*-infected dogs prior to producing hybridoma cell lines and monoclonal antibodies specific for such antigens.

A counterimmunoelectrophoresis (CIE) technique was employed as an assay for the circulating antigens. CIE was performed essentially as described by Siber and Shapriwsky (J. Clin. Microbiol., 7:392-393, 1978) with minor modifications. It was found that parasite antigens present in infected dog sera were still detectable after the sera were heated to 100° C. for 30 minutes or after extraction with an equal volume of 30% trichloroacetic acid (TCA) followed by extensive dialysis against 0.01M phosphate buffered saline, pH 7.2 (PBS). Antigenic activity was also maintained after extraction of sera with 2M perchloric acid (neutralized with KOH and dialyzed vs. PBS) These characteristics suggested that the antigens of interest were glycoproteins with a high carbohydrate content. Since the antigens of interest would be present in a TCA and heat treated preparation of an extract prepared from adult worms, it was decided that this TCA and heated preparation would be simpler to work with than the whole-worm extract.

For antigen preparation, thawed adult worms or lyophilized *D. immitis* microfilariae, isolated as described by Weil et al. (Am. J. Trop. Med. Hyg., 31:477-485, 1982), were ground in a mortar and pestle and extracted overnight 5n PBS at 4° C. Particulate matter was sedimented by sequential centrifugations at 2000×g for 15 minutes and 2 hours at 10,000×g. The supernatant was sterilized by filtration through a 0.45 micron filter and frozen at −70° C. Protein determination was performed according to Lowry et al. (J. Biol. Chem., 103:265-275, 1951).

Figure 1:
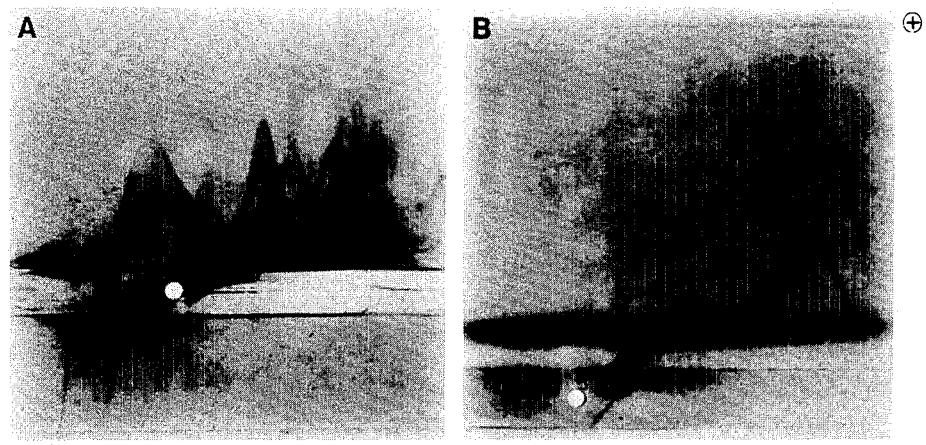
FIG. 1 depicts the results of crossed immunoelectrophoresis of *Dirofilaria immitis* antigens vs. rabbit anti-*D. immitis*. A. - *D. immitis* adult worm extract B. - DATH (TCA and heat treated antigenic extract)

FIG. 1 shows crossed immunoelectrophoresis patterns (see B. Weeke in "Quantitative Electrophoresis", N. Axelsen et al., eds., Universitetsforlaget, Oslo, 1973, 49-59) of PBS-extracted adult worm antigens prepared as described above with at least 25 major antigens and the TCA and heat treated extract (hereafter "DATH") with three major precipitation arcs and several minor ones. DATH contains both carbohydrate (30%, phenol-sulfuric acid method) and protein (70%, Lowry method). In addition, TCA and heat were employed to precipitate proteins from *D. immitis*-infected dog serum to partially purify the circulating parasite antigens. Infected dog serum was extracted with an equal volume of 30% TCA, extensively dialyzed against PBS, and heated to 100° C. for 30 minutes before being centrifuged at 4000×g for 20 minutes. The supernatant was concentrated by membrane filtration.

Figure 2:
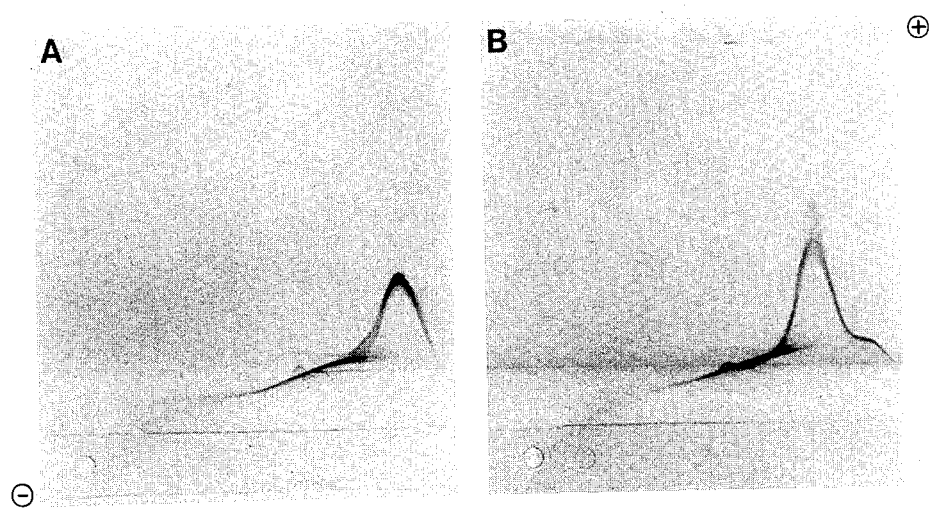
FIG. 2 depicts the results of immunoelectrophoresis showing that parasite antigen derived from dog serum is present in DATH.

Next, several procedures were carried out to identify which of the worm antigens present in the DATH preparation were present in the blood of infected dogs. First, dog serum-derived parasite antigen was run in crossed immunoelectrophoresis against rabbit anti-*D. immitis* antisera and two arcs were identified and compared with the crossed immunoelectrophoresis pattern of the worm-derived DATH preparation for distance migrated relative to albumin and shape of the arcs. Immunochemical identity of the serum-derived and worm-derived antigens was further established by fusion of arcs in tandem crossed immunoelectrophoresis (J. Kroll, in "Quantitative Electrophoresis", op cit., 60-61) (see FIG. 2). Secondly, the techniques of rocket-line electrophoresis and crossed-line immunoelectrophoresis (N. Axelsen et al., in "Quantitative Electrophoresis", ibid., 91-94) were used to demonstrate immunochemical identity between antigens derived from infected dog serum and the parasite (see FIG. 3), and the former technique was used to assay for the presence of the antigens of interest in subsequent studies.

These studies showed that infected dog sera contained two parasite antigens and that these antigens migrated towards the anode at pH 8.6 with migration distances relative to albumin of 1.1 and 1.0. These antigens, the top two antigen lines in line electrophoresis of DATH against the rabbit anti-*D. immitis* antisera, are referred to herein as Rover 1 and Rover 2, respectively.

Studies performed with Rover 1 and 2 (whether derived from infected dog serum or from adult *D. immitis* worms) showed that the antigenic activity of both antigens was maintained after ether extraction (the antigens remaining in the aqueous phase), but partially lost after exposure to either trypsin or pronase (each 1 mg/ml in Hank's balanced salt solution for nine hours at 37° C.). Antigen activity was lost after treatment of the serum-derived antigen with sodium metaperiodate (0.25M, 5° C. for 2 hours, followed by dialysis).

DATH was analyzed by gel filtration to determine the molecular weights of Rover 1 and Rover 2; fractions were monitored for antigen content by rocket-line electrophoresis. Representative results are shown in FIG. 4. Rover 1 eluted between ferritin and blue dextran on a "Sephacryl S300" (Pharmacia Fine Chemicals, Piscataway, N.J.) column (50×1 cm, buffer 0.01M PBS, pH 7.2) and Rover 2 eluted in 2 peaks, one with Rover 1 and the other at a slightly lower apparent molecular weight. This result suggests an apparent molecular weight of greater than 500,000 daltons for Rover 1 and the heavy peak of Rover 2.

DATH was also analyzed by SDS-polyacrylamide gel (SDS-PAGE) electrophoresis (U. Laemmli, Nature, 227:680, 1970) (See FIG. 5). No bands were seen when the gels were stained with the protein stain Coomassie blue, but when the gels were stained for carbohydrate with PAS, a diffuse band of high molecular weight material was observed. It is not known where Rover 1 or Rover 2 are in the SDS-PAGE pattern. They have high apparent molecular weights by gel filtration and high molecular weight glycoproteins might be expected to produce a broad PAS positive band near the origin in a 5% SDS-PAGE gel. However, these results may not reflect the true molecular weights of these molecules as it is well known that heavily glycosylated glycoproteins behave anomalously in SDS-PAGE and gel filtration.

As the antigens of interest did not migrate satisfactorily in polyacrylamide gel but obviously migrated well in agarose, isoelectric focusing of DATH was performed in agarose and the migration of the antigens was revealed by electrophoresing the focused agarose strip into an antibody containing gel with a line electrophoresis (see FIG. 6). This technique is a combination of crossed line electrophoresis and isoelectrofocusing. By this technique, Rover 1 and Rover 2 both have isoelectric points of less than 4.

It was thus found that two parasite antigens were present in the serum of *D. immitis* infected dogs, namely, Rover 1 and Rover 2. These antigens appeared to be anodic high molecular weight glycoproteins that were not destroyed by TCA extraction or mild heat treatment (100° C. for 30 minutes), and they have isoelectric points of less than 4. These characteristics clearly distinguish these antigens from the circulating onchocerciasis antigen described by Ouassi et al. and Des Moutis et al., supra.

Mouse Immunization and Hybridoma Selection

BALB/c mice were immunized by intraperitoneal injection with DATH in complete Freund's adjuvant on days 1 and 30. Mice were bled one week after the boost immunization and sera were tested for antibodies by enzyme immunoassay (ELISA) (first described by E. Engvall and P. Perlmann, Immunochemistry, 8:871, 1971; and modified for measurement of antibodies to *D. immitis* as described by Weil et al., Experimental Parasitology, 51:80, 1981).

Microtiter plates were precoated with DATH (5 ug/mL in carbonate buffer, pH 9.6) and blocked with PBS with 1% BSA. Diluted sera were added to the washed microtiter plates and incubated at 37° C. for 30 minutes. After washing the plates with PBS with 0.05% "Tween 20", alkaline phosphatase conjugated goat anti-mouse immunoglobulin was added to the plates and incubated 30 minutes at 37° C. After washing, bound enzyme was revealed by adding diethanolamine substrate and incubating for 30 minutes at room temperature. The reaction was stopped with 2M NaOH and the absorbance at 405 nm of the product was measured with an ELISA reader (Dynatech Laboratories, Alexandria, Va.). The two mice with the best antibody titers were chosen for fusion. They were boosted once more with DATH by intraperitoneal injection without adjuvant. Four days later their spleens were harvested and spleen cells were fused with NS-1 myeloma cells by standard techniques (as described by G. Galfre et al., Nature, 266:550, 1977), and the cells were distributed into 96 well cell culture plates and cultured. After two weeks, supernatants from these cultures were tested for antibody production to the DATH antigen as described for mouse serum above.

Positive wells were tested for antibody to the specific antigens that circulate in infected dog sera by a novel counterimmunoelectrophoresis (CIE) inhibition technique. Circulating antigen derived from infected dog sera as described above was incubated with culture supernatants for 30 minutes at 37° C., centrifuged at 16,000×g for two minutes, and the supernatant was tested for parasite antigen activity by counterimmunoelectrophoresis against rabbit anti-*D. immitis* antiserum as described. The presence of desired antibodies in culture supernatants was revealed by the ability to inhibit the formation of the precipitin reaction normally observed when the serum-derived parasite antigen alone or antigen premixed with control supernatants were electrophoresed against the rabbit antiserum. Cells from antibody producing wells were cloned in agar (by the technique of Coffino et al., Journal of Cellular Physiology, 79:429, 1972). Culture supernatants from these clones were screened for specific antibody production by the same two-stage (ELISA and CIE inhibition) procedure described above.

Characterization of Monoclonal Antibodies

Isotypes of antibodies produced in vitro by cloned cell lines were determined by ELISA inhibition (see Halliday and Wisdom, FEB Letters, 96:298, 1978) using purified mouse monoclonals of known isotype and isotypespecific antisera as previously described (Scott and Fleishman, Journal of Immunology, 128:2622, 1982). Each cell culture supernatant contained antibodies of a single isotype, which is indirect evidence of monoclonality. Four monoclonal antibodies were chosen for further study. Two were of the $IgG_1$ isotype (designated "1418BA10.1" and "1418BF2.1") and two were of the IgM isotype (designated "1419DB6.2" and "1419BA12.1"). Antibodies for further characterization were obtained by intraperitoneal injection of hybridoma cells into pristane-primed mice and tapping 10 days later as described by Edwards (Biochemical Journal, 200:1, 1981). Globulins were precipitated from ascites fluids with ammonium sulfate. For some experiments, $IgG_1$ monoclonals were further purified by DEAE chromatography and the monoclonality of these preparations was demonstrated by isoelectric focusing in agarose (see, for example, FIG. 7). The $IgG_1$ and IgM monoclonals, used alone or in combination, failed to form precipitin lines with *D. immitis* antigens in CIE or other precipitation techniques. The $IgG_1$ monoclonals failed to bind to staphylococcal Protein A-Sepharose (Pharmacia) with the method described by Ey et al. (Immunochemistry, 15:429, 1978).

Antigen specificity of monoclonal antibodies was assessed by affinity chromatography and by immunoprecipitation. Thus, for example, monoclonal antibody 1418BF2.1 was coupled to CNBr-Sepharose 4B beads (Pharmacia) according to the manufacturer's instructions, with a measured coupling efficiency of over 90%. DATH worm antigen was incubated with the beads for 16 hours to allow the antibody to bind to the worm antigen. The beads were then extensively washed with PBS, with 0.1% "Triton ×100" and 0.5M NaSCN to remove unbound antigen. Bound antigens were eluted with 3.5M NaSCN, dialyzed against PBS, and concentrated by membrane filtration to the volume of antigen applied to the beads. Eluted antigens were analyzed by rocket line electrophoresis (see FIG. 8) which showed that Rover 1 and Rover 2 bound specifically to the beads. The technique of indirect immunoprecipitation was also used to further assess antigen specificity of the monoclonals. The monoclonal antibodies (ascites globulin preparations) were first incubated with DATH or *D. immitis* adult antigens overnight at 4° C. Immune complexes were precipitated with sheep anti-mouse IgG or sheep anti-mouse IgM antibodies (Cappel Laboratories), depending on the isotype of the monoclonal antibody being tested. Immune complexes were washed twice with PBS with 1% BSA, and antigen was freed from the complexes by heat treatment (100° C. for five minutes for DATH, 80° C. for five minutes for *D. immitis* adult antigens). Supernatants were tested for antigen content by rocket-line electrophoresis (FIG. 8). Control immunoprecipitates were prepared exactly as above except that normal mouse serum was substituted for monoclonal antibody. Control precipitates did not contain worm antigens while precipitates prepared with monoclonal antibodies contained both Rover 1 and Rover 2. As illustrated by FIG. 8, monoclonal 1418BF2.1 appeared to bind Rover 2 better than Rover 1, while monoclonal 1419BA12.1 appeared to bind both antigens equally well. Thus, Rover 1 and Rover 2 appear to share the epitopes recognized by monoclonals 1418BF2.1 and 1419BA12.1, but these epitopes may not be equally represented on both antigens.

Inhibition studies were performed to examine epitope specificity of the monoclonal antibodies by techniques modified from M. Nomura et al. (Journal of Immunological Methods, 58:293, 1983). Monoclonal antibodies were biotinylated with biotin N-hydroxysuccinimide (E-Y Laboratories, San Mateo Calif.) by the method of J. Guesdon et al. (The Journal of Histochemistry and Cytochemistry, 27:1131, 1979). Optimal dilutions of these directly labeled preparations were added to DATH-sensitized microtiter plates and incubated at 37° C. for 30 minutes. Binding of the monoclonals was detected (after washing) by sequentially adding avidin-peroxidase (Cappel Laboratories) for 30 minutes at 37° C. followed by (again after washing) the substrate O-phenylene diamine (30 minutes at 25° C.) and measuring the optical density of the colored product at 490 nm. Epitope specificity was determined by diluting unlabeled monoclonals across the plate and incubating for 30 minutes before adding the biotinylated monoclonals to the plates. All combinations of the four monoclonals were tested in this manner and representative results are shown in FIG. 9. Binding of the biotin-labeled monoclonals was inhibited by preincubation of the plate with the same monoclonal, as expected. In addition, complete cross-inhibition was observed between the two monoclonals of the IgM isotype and between the two IgG$_1$ monoclonals, but not between any IgG$_1$ and IgM monoclonal pair. These results suggest that the two IgG$_1$ monoclonals recognize the same epitope and that the epitope is different from that recognized by the two IgM monoclonals. Although these monoclonals were derived from separate wells from the original fusion, it is possible but unlikely that the two IgG$_1$ and IgM monoclonals are identical.

Use of Monoclonal Antibodies to Detect *D. Immitis* Antigens in Sera from Infected Dogs Sera were obtained from experimentally infected dogs, naturally infected dogs and uninfected dogs. The infection status of these dogs was assessed by blood examination for microfilariae and by necropsy. A number of different methods, all involving variations of the sandwich ELISA technique, were used to detect parasite antigens in sera from infected dogs. The assay was divided into an antigen trapping step and an antigen detection step. It was found that antigen trapping could be done with either polyvalent rabbit antiserum or with monoclonal antibodies. All possible combinations of monoclonals were tried for the trapping and detection steps. Interestingly, the best results were obtained with the use of a single monoclonal for both trapping and detection steps. Obviously, the epitope being detected must be repeated many times on the circulating antigen. For purposes of illustration, one form of the assay is described below in detail.

Microtiter plates were sensitized by incubating 100 ul of monoclonal 1418BF2.1 (ascites globulin preparation, 10 ug protein/ml) in 0.1M NaHCO$_3$, pH 8.0. overnight at 37° C. Dog sera were pretreated to free parasite antigen from immune complexes by diluting with an equal volume of 0.1M disodium EDTA (pH 7.6) and heating to 100° C. for five minutes, followed by centrifugation at 16,000×g for 5 minutes. Serum supernatants (100 ul) were added to microtiter plates, serially diluted with PBS, with 0.1% "Tween 20" and 2% heat inactivated fetal calf serum (FCS), and incubated at 37° C. for 120 minutes. After washing the plates, an optimal dilution of biotinylated monoclonal 1418BF2.1 (diluted in PBS/"Tween 20"/5% FCS) was added to the plates and incubated for one hour. After washing, 100 ul peroxidase-conjugated avidin diluted in PBS/"Tween 20"/5% FCS was added and incubated for one hour at 37° C. After again washing, 100 ul substrate O-phenylene diamine was added. The enzyme reaction was stopped after 30 minutes with 50 ul of 8M H$_2$SO$_4$, and the optical density of the colored product was measured at 490 nm. A standard titration curve of DATH antigen in normal dog serum (also treated with EDTA and heat) was included on each plate. The concentration of circulating antigen in test sera is derived from the standard curve and expressed as units equivalent to the antigen content of 1 ng/ml (protein, determined as described by Lowry et al., Journal of Biological Chemistry, 103:265. 1951) of DATH antigen. The sensitivity of the assay is 4 units, the amount of the circulating antigen present in 4 ng (protein) of DATH antigen. A representative standard curve for the assay is shown in FIG. 10.

The results of the assay for sera from dogs with autopsy-verified infections are shown in the following Table I:

TABLE I

| DETECTION OF CIRCULATING *DIROFILIARIA IMMITIS* ANTIGEN IN INFECTED AND CONTROL DOGS | | |
|---|---|---|
|  | N | % Positive |
| *D. immitis* infected |  |  |
| Microfilaremic | 19 | 100 |
| Amicrofilaremic | 08 | 100 |
| Uninfected |  |  |

TABLE I-continued
DETECTION OF CIRCULATING DIROFILIARIA IMMITIS ANTIGEN IN INFECTED AND CONTROL DOGS

|  | N | % Positive |
|---|---|---|
| Unexposed to parasite | 10 | 0 |
| Naturally exposed to parasite | 16 | 0 |
| *Dipetalonema reconditum* infected | 13 | 0 |

The sensitivity of the assay wa 100% for these sera (from both microfilaremic and amicrofilaremic infected dogs), and the specificity of the assay was 100%. Sera from dogs infected with the filarial parasite *Dipetalonema reconditum* but not with *D. immitis* were negative in the assay. The amount of parasite antigen present in infected dog sera correlated significantly with the number of female worms recovered at necropsy for 23 dogs (Pearson correlation coefficient, $r=0.70$, P less than 0.001; see FIG. 11). This relationship adds to the clinical utility of the assay.

The advantages of the ELISA assay with the monoclonal antibodies of the invention over the counterimmunoelectrophoresis assay may be summarized as (a) it is somewhat more sensitive (by a factor of 4 for the assay of the invention); (b) the monoclonal antibodies are reagents that can be standardized and produced without immunization of animals with worm antigen; (c) more samples can be handled with the ELISA assay and results can be absolutely quantified relative to a worm antigen standard. Counterimmunoelectrophoresis, on the other hand, is a semiquantitative technique.

EXAMPLE 2

Example 1 was repeated and amplified with the following results to further characterize my monoclonal antibodies and circulating parasite antigens in sera from *Dirofilaria immitis* infected dogs and to further illustrate the use of my assay to detect *D. immitis* antigens in infected dog sera. The TCA and heat treated extract referred to in Example 1 as "DATH" is referred to in this Example 2 as "DiA-TCA/heat".

Localization of tissue binding sites for monoclonal antibodies was done with an immunoperoxidase technique. Previously frozen *D. immitis* adult worms were fixed overnight in Rossman's fixative (Alan et al., J. Exp. Med. 92:35, 1950), embedded in paraffin, sectioned, and mounted on glass microscope slides. Some of the sections were stained with hematoxylin and eosin or periodic acid Schiff for orientation. Other sections were deparaffinized, rinsed with PBS, and flooded with an appropriate dilution of biotinylated monoclonal diluted in PBS/T/FCS for 30 min at 37° C. Slides were washed with PBS/T and layered with avidin-conjugated peroxidase in PBS/T/FCS for 30 min at 37° C. After washing, the slides were developed with the substrate diaminobenzidine (Pfaltz and Bauer, Inc., Stamford, Conn.) for 20 min at room temperature. Controls included slides treated with (a) normal mouse serum with avidin peroxidase and substrate, (b) avidin peroxidase and substrate, and (c) substrate alone. The enzyme reaction was stopped by rinsing the slides with water. Microfilariae, isolated as described by Weil et al. (Exp. Parasitol., 51:80, 1981), were stained in suspension by a slight modification of the technique used for worm sections. Mounted slides were examined with an Olympus BH microscope (Olympus Corp., New Hyde Park, N.Y.) and photographed with Tri-X film (Eastman Kodak).

Antigen Assay

Different configurations were tried for the assay of circulating parasite antigen in dog sera, including the use of polyclonal antiserum and monoclonals, singly and in combination, for antigen trapping and detection steps. The optimal working dilution for each reagent was determined by block titration studies. The effect of time on each incubation step was also examined. The studies in Example 1 indicated that parasite antigens in dog sera are often hidden within complexes. Therefore, a number of different methods were evaluated for freeing these antigens from complexes without destroying them and without increasing background values for the assay. The following procedure is illustrative: Polyvinyl microtiter plates (Dynatech) were sensitized overnight at 37° C. with 100 ul/well monoclonal antibody 1418 BF2.1 diluted to 10 ug/ml in 0.1M $NaHCO_3$, pH 8.0. Parasite antigen in dog sera was measured relative to a DiA-TCA/heat standard diluted to 10 ug/ml (protein) in PBS, frozen in aliquots, and included on each ELISA plate in every run. Sera and antigen standard in 50% normal dog serum were pretreated by adding an equal volume of 0.1 M disodium EDTA (Sigma), pH 7.5, and heating to 100° C. for 5 min followed by centrifugation for 5 min at $16,000 \times G$. Pretreated sera and antigen standard were added to sensitized microtiter plates, and twofold dilutions were carried out in PBS/T/FCS with a final volume per well of 50 ul. Preliminary experiments showed that antigen was equally detectable when diluted in PBS, PBS with 5% FCS, or in normal dog serum up to a concentration of 50%. Sera were incubated on the plates for 2 hr at 37° C. Plates were washed with PBS/T, and 100 ul of an appropriate dilution of biotinylated monoclonal 1418 BF2.1 were added in PBS/T/FCS, and the mixture was incubated at 37° C. for 1 hr. After washing, 100 ul avidin peroxidase diluted in PBS/T/FCS were added for 1 hr at 37° C. The substrate used was o-phenylenediamine, and the reaction was stopped after 10 min. with 50 ul of 8M $H_2SO_4$. Optical density was read vs. a PBS blank at 490 nm with an ELISA reader. The standard curve was plotted on semilog paper and antigen content in test sera was interpolated relative to the standard. Data analysis was performed with a statistics program on an IBM-PC computer.

Dog Sera

Sera was obtained from 23 dogs that were experimentally infected with *D. immitis* and from 10 dogs that were never exposed to the parasite. Other sera were taken from naturally infected dogs, *Dipetalonema reconditum*-infected dogs, and uninfected-but-naturally exposed dogs. All sera (excluding sera for the time course study) were obtained by venipuncture 3 mo. or less before the dogs were sacrificed. All dogs were necropsied and carefully examined for the presence of *D. immitis* in the heart, vena cavae, and pulmonary arteries. Worm counts by sex were available for 41 of the 46 infected dogs.

Results

As in Example 1, two of the monoclonals (designated "1418BF2.1" and "1418BA10.1") were of the $IgG_1$ isotype and two (designated "1419B12.1" and "1419DB6.2") were of the IgM isotype.

Immunoperoxidase studies were performed as described above with monoclonals 1418BF2.1 and 1419BA12.1 (representing the two epitope specificities) in order to localize Rover 1 and Rover 2 in *D. immitis*. Both monoclonals produced the same results. Binding was observed in a number of sites. The cuticle, intestine, and coelomic cavity of both male and female adult worms were moderately reactive. Very strong labeling was observed in the female uterine wall and in the eggs, including both the egg contents and the vitelline membrane (see FIG. 12). Intact microfilareae did not bind the monoclonals, but fragmented or damaged microfilariae were positive. All controls were negative.

As described above, dog sera were tested for the presence of parasite antigen by a direct sandwich ELISA technique. A representative titration curve for the standard, DiA-TCA/heat in normal dog serum is similar to that shown in FIG. 10. The curve was linear for antigen doses between 10 and 100 ng/ml. The sensitivity of the assay was 4 ng/ml (protein content) of the untreated standard, which corresponds to 2 ng/ml (or 0.1 ng of standard) actually tested on the plate. This antigen dose produced an optical density three standard deviations above the mean of 10 negative dog sera. Titration curves of sera from *D. immitis*-infected dogs were parallel to the standard with interdilutional coefficients of variation for three serum dilutions of 15%. Intraassay reproducibility (10 sera tested in duplicate on the same day was 12% and interassay reproducibility (10 sera tested on three different days) was 15%.

The cumulative or overall results obtained with dog sera assayed in Examples 1 and 2 are shown in the following Table IA.

TABLE IA

SENSITIVITY AND SPECIFICITY OF *DIROFILARIA IMMITIS* ANTIGEN ASSAY

| Infection status of dogs | +/Total | % Positive |
|---|---|---|
| *D. immitis*, microfilaremia present | 36/37 | 97 |
| *D. immitis*, microfilaremia absent | 9/9 | 100 |
| Total, *D. immitis*-infected | 45/46 | 98 |
| *D. reconditum*-infected | 0/20 | 0 |
| Uninfected | 0/26 | 0 |

Forty-five of 46 sera from infected dogs (including nine dogs with amicrofilaremic mature infections) were positive in the assay. Worm recoveries in these dogs ranged from 0 (dog with *D. immitis* microfilaremia) to 146. The false negative was obtained from a microfilaremic dog that had two worms recovered at necropsy (one of each sex). Parasite antigen was not detected in sera from uninfected dogs regardless of their exposure history. Sera from dogs infected with the filarial worm *Dipetalonema reconditum* were also negative in the test. Antigen levels for positive sera from infected dogs varied from 15 to 652 ng/ml of the standard. Antigen levels correlated significantly with the total number of adult worms recovered at necropsy (r=0.69), but the best correlation was observed between antigen content and the number of adult female worms recovered (r=0.82, p 0.001).

As to parasite specificity, the antigen assay did not detect parasite antigen in sera from dogs infected with the filarial nematode *Dipetalonema reconditum* (n=20), or in sera from humans infected with *Wuchereria bancrofti* (n=5) or *Onchocerca volvulus* (n=5).

The time course of parasite antigenemia was studied with sera from eight dogs that were experimentally infected with *D. immitis*. The data were expressed as the percentage of the maximum antigen content observed for each individual dog (see FIG. 13). Parasite antigen was first detected 6 mo. after infection, just prior to the onset of microfilarial patency. Antigen levels increased from 6 to 9 mo. after infection, but remained fairly stable during the subsequent period of observation out to 21 mo. Thus, the presence of *D. immitis* antigen in dog serum indicates the presence of adult parasites in dogs. The diagnostic utility (sensitivity and specificity) of the described monoclonal antibody-based assay is far superior to previously described tests for canine dirofilariasis which are based on the measurement of antibody to parasite antigens. Antibody tests for this parasitic infection have shown poor specificity (Weil, et al., Fed. Proc. 42:Abstr. 3281, 1983). In addition, the sensitivity of the assay of this invention is superior to previous methods for antigen detection in *D. immitis* such as that described by Tagawa et al., Proc. Natl. Acad. Sci. (USA) 76:4530 (1979). The sensitivity of the monoclonal antibody-based ELISA is about six-fold better than that of the counterimmunoelectrophoresis assay for the same antigens (Weil et al., Am. J. Trop. Med. Hyg., 33:425, 1984).

EXAMPLE 3

Demonstration of parasite antigen in infected dog serum by the immunoblot technique with polyclonal and monoclonal antibodies employed the following procedure:

Immunoblot analysis: For sodium dodecyl sulfatepolyacrylamide gel electrophoresis (SDS-PAGE) (Laemmli, supra), parasite antigens, antigens bound to anti-*D. immitis* Sepharose beads, and molecular weight standards (Biorad Laboratories) were boiled in sample buffer for one minute and electrophoresed in 5–15% gradient 0.8 mm minigels as described by Matsudaira and Burgess (Anal. Biochem., 87:386) (100 V, 50 min). Gels were soaked in transfer buffer (0.025M Tris, 0.193M glycine, 20% methanol, pH 8.35) 30 min. and electrophoretically transferred to nitrocellulose membrane (BA85, Schleicher and Schuell, Keene, N.H.) essentially as described by Towbin et al. (Proc. Natl. Acad. Sci. USA, 76(9):4350) with a Transblot apparatus (Biorad Laboratories) (4° C., 150 V, 90 min). After transfer, nitrocellulose membranes were stained for protein with amido black or placed into 2% nonfat dry milk in PBS overnight at 4° C. to block remaining protein binding sites. The presence of parasite antigens on nitrocellulose membranes was demonstrated by enzyme immunoassay. Papers were incubated in biotinylated rabbit anti-*D. immitis* antibodies diluted in PBS with 0.05% Tween 20 (Sigma) and 5% fetal calf serum (PBS/T/FCS) for one hour, washed three times with PBS/T, incubated in peroxidase conjugated avidin (Cooper Biomedical, Inc., Malvern, Pa.) diluted in PBS/T/FCS for 30 min at 37° C. and washed three times in PBS/T. Other papers were treated with horseradish peroxidase (Sigma) conjugated (15) monoclonal antibody 1418BF2.1 diluted in PBS/T/FCS for one hour, followed by extensive washing in PBS/T Membranes were flooded with 3,3'-diaminobenzidine (Sigma) substrate for 5–10 min, and the reaction was stopped by rinsing papers in water.

Several parasite antigens were identified in infected dog sera by the immunoblot method with rabbit anti-*D. immitis* antibodies and monoclonal antibody 1418BF2.1 which is used in our assay for *D. immitis* antigen in dog sera (see FIGS. 14A and 14B). These included a well-defined high molecular weight band and a broad high molecular weight smear with superimposed bands with apparent molecular weights of 165, 140, 110, 68 and 60 kD. Similar bands were identified in the female ES preparation. The 68 and 60 kD bands identified in dog sera may not entirely represent parasite antigens. Similar bands were also present in uninfected dog sera. These were labeled by rabbit anti-*D. immitis* antibodies but not by monoclonal 1418BF2.1. Unstained bands present in all lanes were caused by rabbit serum proteins that were released from the affinity beads when the beads were boiled in sample buffer.

EXAMPLE 4

Circulating parasite antigens contain phosphoryl choline.

Phosphoryl choline is an antigen determinant present in various microorganisms that has been the subject of intense immunological research (reviewed in Claflin et al., The murine antibody response to phosphocholine, The Biology of Idiotypes, Plenum Press, N.Y., 1984). Because phosphoryl choline is known to be present on helminth antigens from a number of nematode species (Pery et al. Eur. J. Immunol., 4:637, 1974), the ability of phosphoryl choline to inhibit binding of the above-noted monoclonal antibodies to DATH was examined. The antigen was bound to polyvinyl microtiter plates by passive absorption. Binding of a fixed dilution of monoclonal antibody to the antigen on the plate was measured in the presence of various concentrations of phosphoryl choline (Sigma Chemical Co.). Phosphoryl choline inhibited the binding of monoclonal antibodies 1419DB6.2 and 1419BA12.1, but not 1418BF2.1 or 1418BA10.1. The phosphocholine specificity of monoclonals 1419DB6.2 and 1419BA12.1 was further established by the finding that they bound to phosphocholine-conjugated bovine serum albumin (BSA) but not to unconjugated BSA in ELISA. It was also found that phosphocholine-specific monoclonal antibodies such as TEPC-15 (Claflin et al., supra) could be substituted for the above-noted monoclonal antibodies to detect parasite antigen in infected dog sera as previously described above. These results indicate that the circulating *D. immitis* antigens contain phosphocholine determinants and that the antigens can be detected with antiphosphocholine antibodies including TEPC-15, 1419DB6.2 and 1419BA12.1. Monoclonal antibodies 1418BF2.1 and 1418BA10.1 that bind to the circulating antigens are not specific for phosphocholine. Thus, while the circulating antigens do contain phosphocholine determinants, they also have other determinants which are unknown.

EXAMPLE 5

The monoclonal antibodies bind to epitopes that are present on many *D. immitis* antigens including the circulating antigens as shown by the following.

*D. immitis* adult worm extract was subjected to SDS-PAGE followed by electrophoretic transfer to nitrocellulose as described by Towbin et al., supra. Strips of nitrocellulose were exposed to monoclonal antibodies and binding of monoclonals was revealed by paper ELISA as described above. All of the monoclonal antibodies tested (i.e. 1418BF2.1, 1419BA12.1, 1419DB6.2 and 1418BA10.1) bound to multiple antigens in the adult worm extract as shown in FIG. 15. Thus, these monoclonal antibodies bind to epitopes that are present on many *D. immitis* antigens including those that are found in the blood of infected dogs. The two IgG$_1$ monoclonal antibodies, 1418BF2.1 and 1418BA10.1, produced identical patterns which were different from that produced by the IgM monoclonal antibodies 1419DB6.2 and 1419BA12.1. This result is consistent with the epitope specificity studies set forth above.

EXAMPLE 6

Antigens produced in vitro by *D. immitis* (ES): Live *D. immitis* adult worms were washed in PBS, placed in sterile culture flasks containing RPMI-1640 (provided by the Washington University Cancer Center) supplemented with 50 U/ml penicillin G and 50 ug/ml streptomycin, and incubated at 37° C. in 5% $CO_2$/air. Medium was changed daily for two days. Culture supernatants were passed through 0.45 uM filters, lyophilized, and dialyzed vs. PBS. Microfilarial ES was produced by *D. immitis* MF isolated as previously described. Microfilariae were maintained at a concentration of 100,000/ml in RPMI with penicillin and streptomycin for 16 h at 37° C. Medium recovered by centrifugation (1000×g for 20 min) was filtered, lyophilized and dialyzed vs. PBS.

DiA-TCA/heat in 0.1M acetate buffer, pH 4.0, was added to DEAE-cellulose (DE52, Whatman, Maidenstone, Kent, UK) equilibrated in the same buffer and packed in a small column. The DE52 was washed with acetate buffer and eluted with a 0–1.1M NaCl gradient in acetate buffer. Eluted fractions that contained the antigens of interest (assessed by rocket-line immunoelectrophoresis) were pooled, dialyzed vs. PBS and concentrated by vacuum filtration.

To assess the stability of the circulating antigens, DiA-TCA/heat and TCA/heat treated infected dog sera were subjected to ether extraction, trypsin (Worthington Biochemical Corp., Freehold, N.J.) 1 mg/ml in Hank's balanced salt solution (HBSS, Washington University Cancer Center) at 37° C., and sodium metaperiodate (Sigma, 0.25M, 4° C. for 2 hr) treatments. Enzyme treatments were terminated by heating to 100° C. for 5 min. Periodate oxidation was followed by dialysis vs. PBS and concentration to the starting volume. Protein content was measured as described by Lowry supra, vs. a bovine serum albumin standard. Neutral sugars were measured by the phenol sulfuric acid method (Hodge et al. 1962, Determination of reducing sugars and carbohydrates in methods of carbohydrate chemistry, Vol. I, p. 388–389) with D-glucose (Sigma) as a standard. Uronic acids were measured by the carbazole method (Bitter et al. Anal. Biochem., 4:330, 1962) with glucuronic acid (Sigma) as a standard. Amino sugars were measured with a Beckman 119c amino acid analyzer after hydrolysis with 6N HCl for 4 hours at 105° C. Sulfate was measured by the method of Silvestri et al. (Anal. Biochem. 123:303, 1982). Sialic acid was measured by the thiobarbituric acid method (Downs et al. 1976, Qualitative and Quantitative Determination of Sialic Acids in Methods in Carbohydrate Chemistry, Vol. VII, p. 233–240).

Immunoelectrophoretic techniques

Counterimmunoelectrophoresis was performed as previously described. Crossed immunoelectrophoresis was performed essentially as described by Weeke (Scan. J. Immunol., 2(1):49, 1973). Briefly, *D. immitis* antigens were electrophoresed in 1% agarose (low $M_r$, Biorad Laboratories) in Tris-tricine buffer (9.8 g Tris base, 3.4 g tricine, 0.2 g sodium azide, and 0.106 g calcium lactate/l, pH 8.6) at 10 V/cm at 10° C. until bromphenol blue-labeled boving serum albumin migrated 5 cm (approximately 30 min). After electrophoresis in the first dimension, a one cm lane of agarose containing the electrophoresed antigens was transferred to another plate and electrophoresed into agarose containing rabbit anti-*D. immitis* antibodies for 16 h at 2V/cm, 10° C. After electrophoresis, gels were washed in PBS, stained, and dried. Rocket-line immunoelectrophoresis was performed as previously described. Briefly, DiA-TCA/heat in a narrow agarose strip was electrophoresed into agarose containing rabbit antibodies to *D. immitis* as described above for rocket electrophoresis. Test samples were placed in 2.5 mm wells on the cathodic side of the antigen strip prior to electrophoresis. Parasite antigens from in vitro cultivation or from dog sera cause local antigen excess during electrophoresis such that rockets are superimposed on the line electrophoresis pattern for the corresponding antigens.

Serum-derived parasite antigens produced rocket patterns that formed lines of identity with two lines of the line electrophoresis pattern of DiA-TCA/heat vs. rabbit anti-*D. immitis* antibodies (FIG. 16). These antigens, called Rover 1 and Rover 2, corresponded to the top two antigens seen in line electrophoresis of DiA-TCA/heat vs. immune rabbit serum and they were the two major anodic migrating antigens in the crossed immunoelectrophoretic pattern of DiA-TCA/heat. Rover 1 and Rover 2 were further enriched but not resolved by ion exchange chromatography (FIG. 17). This preparation (DiA-TCA/heat/DEAE) contained 27% protein, 10% neutral sugars, 12% amino sugars, 12% uronic acid, and undetectable (less than 1%) sulfate and sialic acid.

The effects of various treatments on antigenic activity of Rover 1 and 2 as assessed by rocket-line immunoelectrophoresis are shown in Table II below. Immune reactivity of both antigens was maintained after ether extraction and treatment with DNAse, partially lost after prolonged treatment with Trypsin or Pronase, and lost after metaperiodate treatment.

TABLE II

Rover 1 and Rover 2 antigen activity (%) remaining in *Dirofilaria immitis* adult antigen after various treatments as assessed by rocket-line immunoelectrophoresis

|  | Heat | TCA | Pronase | Trypsin | Periodate | DNase | Ether |
|---|---|---|---|---|---|---|---|
| Rover 1 | 100 | 100 | 35 | 75 | 10 | 100 | 100 |
| Rover 2 | 100 | 100 | 35 | 80 | 0 | 100 | 100 |

Rocket-line immunoelectrophoresis was used to estimate the relative concentrations of Rover 1 and 2 per unit protein content in various *D. immitis* antigen preparations (Table III).

TABLE III

Relative Rover 1 and Rover 2 activity[a] in *Dirofilaria immitis* antigen preparations as assessed by rocket-line immunoelectrophoresis

|  | Rover 1 | Rover 2 |
|---|---|---|
| Adult female | 0.19 | 0.17 |
| Adult male | 0.05 | 0.01 |
| MF-somatic | 0.03 | 0 |
| DiA—TCA/heat | 1.0 | 1.0 |
| DiA—TCA/heat/DEAE | 3.08 | 3.3 |
| Female-ES | 0.18 | 0.08 |
| Male-ES | trace | 0 |
| MF-ES | 0 | 0 |

[a]Antigen activity per unit protein relative to DiA—TCA/heat

Both antigens were present in male and female worms as well as microfilariae, but the highest antigen concentrations were observed in the adult female worm preparation. Female-ES contained seven antigens recognized by the rabbit anti-*D. immitis* antibodies including Rover 1 and 2 (FIG. 16 and Table III). Male-ES contained a trace of Rover 1 but no Rover 2. Neither Rover 1 nor Rover 2 were detectable by this technique in MF-ES.

The same antigens were analyzed for circulating antigen content by ELISA (Table IV). The content of monoclonal antibody-reactive antigens per microgram protein in *D. immitis* antigen preparations (relative to the DiA-TCA/heat standard, 1000 ng/ug) was determined by ELISA as described in Example 2.

TABLE IV

"Circulating antigen" content in *Dirofilaria immitis* antigen preparations

| Antigen Preparation | "Circulating Antigen" Content/ug Protein[a] | Enrichment |
|---|---|---|
| *D. immitis* adult, mixed(DiA) | 263 | 1 |
| DiA—TCA/heat (batch 7) | 1440 | 5.5 |
| DiA—TCA/heat/DEAE | 4291 | 16.3 |
| Adult male | 63 |  |
| Adult female | 390 |  |
| MF, somatic | 6.7 |  |
| Male-ES | 2[b] |  |
| Female-ES | 478[c] |  |
| MF-ES | 0.14[d] |  |

[a]Measured by monoclonal antibody-based enzyme immunoassay relative to a DIA—TCA/heat standard (batch 6), 1000 U/ug protein.
[b]8.3 ug ES protein and 16.75 antigen units/male worm/day.
[c]17.1 ug ES protein and 8185 antigen units/female worm/day.
[d]165 ug ES protein and 22.5 antigen units/$10^6$ MF/day.
ES, excretory-secretory products
MF, microfilaria These results indicate that the epitope which is recognized by monoclonal antibody 1418BF2.1, which is a component of the circulating *D. immitis* antigens detected by this assay, is present in adult female and male worms as well as MF. However, the epitope is particularly strongly represented in adult female worms. The epitope was also present in all of the ES preparations, but much more was produced by adult females than by adult males or MF, both in terms of antigen produced per day per worm and antigen content per ug protein released in vitro. Partial purification of the DIA starting material by TCA/heat treatment and ion exchange chromatography resulted in a 16-fold enrichment for the epitope defined by monoclonal 1418BF2.1

Metaperiodate sensitivity of epitopes recognized by monoclonal antibodies to circulating *D. Immitis* antigens

*D. immitis* antigens were incubated with 0.2M sodium metaperiodate for 2 hours at 37° C. or 4° C. followed by extensive dialysis vs PBS. Antigen activity was measured by the monoclonal antibody-based ELISA procedure as described above. Antigen activity was completely ablated by metaperiodate treatment at both temperatures, but unaffected in a control preparation that was incubated with PBS followed by dialysis. Thus, the epitopes or determinants recognized by the monoclonal antibodies of the invention are sensitive to periodate oxidation.

In view of the above, it will be seen that the several objects of the invention are achieved and other advantageous results attained.

As various changes could be made in the above products and methods without departing from the scope of the invention, it is intended that all matter contained in the above description or shown in the accompanying drawings shall be interpreted as illustrative and not in a limiting sense.

What is claimed is:

1. Circulating parasite antigens of *Dirofilaria immitis* essentially purified and isolated from *Dirofilaria immitis* adult worms or infected dog serum treated with trichloroacetic acid and heat, said antigens characterized as follows:
   (a) the antigens being present in *Dirofilaria immitis* worms and in the serum of animals infected with *Dirofilaria immitis*;
   (b) being high molecular weight parasite antigens in infected dog sera as demonstrated by the immunoblot method with polyclonal and monoclonal antibodies;
   (c) not being destroyed by trichloroacetic acid extraction or by perchloric acid extraction;
   (d) not being destroyed by heat treatment at approximately 100° C. for 30 minutes;
   (e) having isoelectric points of under 4 as determined by a combination of ion exchange chromatography and rocket-line immunoelectrophoresis;
   (f) migrating towards the anode at pH 8.6 in agarose gel (10 V/cm) with migration distances relative to albumin of 1.1 and about 1.0 as determined by crossed immunoelectrophoresis;
   (g) forming lines of identity in rocket-line immunoelectrophoresis with soluble acid and heat-stable antigens extracted from adult *D. immitis* worms;
   (h) being a subset of antigens produced in vitro by adult female *D. immitis* worms;
   (i) having a phosphocholine determinant; and
   (j) having determinants whose immunoreactivity is ablated by treatment thereof with sodium metaperiodate.

2. Mono-clonal antibody produced by hybridoma cell lines formed by fusion of cells from a mouse myeloma line and spleen cells from a mouse previously immunized with an antigenic extract prepared from the nematode parasite *Dirofilaria immitis*, which antibody binds to antigenic determinants of circulating parasite antigens of *Dirofilaria immitis* as defined in claim 1 and found in the serum of infected dogs, said antibody being further characterized by binding strongly to the uterine wall and to the eggs of *Dirofilaria immitis* female adult worms.

3. Monoclonal antibody of claim 2 which antibody binds to antigens determinants of circulating antigens of *Dirofilaria immitis* characterized as follows:
   (a) the antigens being present in *Dirofilaria immitis* worms and in the serum of animals infected with *Dirofilaria immitis*;
   (b) being high molecular weight parasite antigens in infected dog sera as demonstrated by the immunoblot method with polyclonal and monoclonal antibodies;
   (c) not being destroyed by trichloroacetic acid extraction or by perchloric acid extraction;
   (d) not being destroyed by heat treatment at approximately 100° C. for 30 minutes;
   (e) having isoelectric points of under 4 as determined by a combination of ion exchange chromatography and rocket-line immunoelectrophoresis;
   (f) migrating towards the anode at pH 8.6 in agarose gel (10 V/cm) with migration distances relative to albumin of 1.1 and about 1.0 as determined by crossed immunoelectrophoresis;
   (g) forming lines of identity in rocket-line immunoelectrophoresis with soluble acid and heat-stable antigens extracted from adult *D. immitis* worms;
   (h) being a subset of antigens produced in vitro by adult female *D. immitis* worms;
   (i) having a phosphocholine determinant; and
   (j) having determinants whose immunoreactivity is ablated by treatment thereof with sodium metaperiodate.

4. A monoclonal antibody of claim 2 which is produced from a hybridoma formed by fusion of NS-1 myeloma cells and spleen cells from a BALB/C mouse previously immunized with an antigenic extract prepared from the nematode parasite *Dirofilaria immitis*.

5. A monoclonal antibody of claim 2 which antibody is specific for phosphoryl choline determinants.

6. A monoclonal antibody of claim 2 characterized in that determinants recognized by said antibody are sensitive to treatment with sodium metaperiodate.

7. An assay method for determining the presence of circulating parasite antigens of *Dirofilaria immitis* in the serum of plasma of *D. immitis*-infected dogs which comprises combining a sample of serum or plasma from a dog infected with *Dirofilaria immitis* and to which no parasite antigen or extract derived from *D. immitis* is added with a first antibody bound to the surface of a solid support, adding thereto a conjugate composed of a second antibody and an enzyme and thereafter adding an enzyme substrate to indicate the presence of absence of said circulating parasite antigens in said sample.

8. An assay method as set forth in claim 7 wherein said first antibody is a polyclonal antibody.

9. An assay method as set forth in claim 8 wherein said second antibody is a monoclonal antibody which specifically binds to determinants present on said circulating parasite antigens.

10. An assay method as set forth in claim 7 wherein said first and second antibodies are monoclonal antibodies which specifically bind to determinants present on said circulating parasite antigens.

11. An assay method for determining the presence of circulating parasite antigens of *Dirofilaria immitis* in the serum of plasma of *D. immitis*-infected dogs which comprises combining a sample of serum or plasma from a dog infected with *Dirofilaria immitis* and to which no parasite antigen or extract derived from *D. immitis* is added with a first monoclonal antibody which specifically binds to determinants present on said circulating parasite antigens, and detecting the presence of said antigens by means of a label on said first antibody or by means of a label on a second antibody added to said first monoclonal antibody, said second antibody specifically binding to said circulating parasite antigens.

12. An assay method as set forth in claim 11 wherein said label is selected from the group consisting of radioactive labels, fluorescent compounds, enzymes, biotin and ferromagnetic labels.

13. An assay method for determining the presence of circulating parasite antigens of *Dirofilaria immitis* as defined in claim 1 in a sample of serum or plasma of a *D. immitis*-infected dog to which no parasite antigen or extract derived from *D. immitis* is added which comprises providing said sample, combining said sample with a monoclonal antibody which binds to antigenic determinants of said circulating parasite antigens of *Dirofilaria immitis* and determining whether said monoclonal antibody binds to said antigenic determinants of said circulating parasite antigens of *Dirofilaria immitis* whereby the presence or absence of said circulating parasite antigens is detected.

14. An assay method for determining the presence of circulating parasite antigens of *Dirofilaria immitis* in a sample of serum or plasma of *D. immitis*-infected dogs to which no parasite antigen or extract derived from *D. immitis* is added which comprises the steps of:

(a) attaching a first antibody to a solid support, said first antibody being a polyclonal antibody which binds to antigenic determinants of said circulating parasite antigens of *Dirofilaria immitis*;

(b) combining said first antibody with said sample of serum or plasma from a dog infected with *Dirofilaria immitis* and a conjugate composed of an enzyme and a monoclonal antibody which binds to antigenic determinants of said circulating parasite antigens of *Dirofilaria immitis* whereby a polyclonal antibody-antigen-conjugated monoclonal antibody sandwich is formed; and (c) thereafter adding an enzyme substrate to said sandwich to colorimetrically indicate the presence or absence of said circulating parasite antigens.

* * * * *

UNITED STATES PATENT AND TRADEMARK OFFICE
CERTIFICATE OF CORRECTION

PATENT NO. : 4,839,275

DATED : June 13, 1989

INVENTOR(S) : Gary J. Weil

It is certified that error appears in the above-identified patent and that said Letters Patent is hereby corrected as shown below:

Column 2, line 20, "al," should read ---al.,---.

Column 2, line 58, "spleeh" should read ---spleen---.

Column 12, lines 20-21, "counterimmmunoelectrophoresis" should read ---counterimmunoelectrophoresis---.

Column 12, line 40, "isotypespecific" should read ---isotype-specific--

Column 15, line 10, "wa" should read ---was---.

Column 16, lines 17-18, "1418 BF2.1" should read ---1418BF2.1---.

Column 16, line 35, "1418 BF2.1" should read ---1418BF2.1---.

Column 17, line 9, "microfilareae" should read ---microfilariae---.

Column 17, line 27, "day was" should read ---day) was---.

Column 18, lines 29-30, "sulfatepolyacrylamide" should read ---sulfate-polyacrylamide---.

Column 19, line 19, "al.," should read ---al.).---.

Column 20, line 68, "boving" should read ---bovine---.

Column 23, claim 2, line 1, "Mono-clonal" should read ---Monoclonal---

Column 24, claim 7, line 3, "serum of plasma" should read ---serum or plasma---.

Column 24, claim 7, line 10, "presence of absence" should read ---presence or absence---.

UNITED STATES PATENT AND TRADEMARK OFFICE
CERTIFICATE OF CORRECTION

PATENT NO. : 4,839,275
DATED : June 13, 1989
INVENTOR(S) : Gary J. Weil

It is certified that error appears in the above-indentified patent and that said Letters Patent is hereby corrected as shown below:

Column 24, claim 11, line 3, "serum of plasma" should read ---serum or plasma---.

Signed and Sealed this

Fifth Day of January, 1999

Attest:

Attesting Officer

*Acting Commissioner of Patents and Trademarks*